United States Patent [19]
Forsell

[11] Patent Number: 6,067,991
[45] Date of Patent: May 30, 2000

[54] MECHANICAL FOOD INTAKE RESTRICTION DEVICE

[76] Inventor: Peter Forsell, Gotalandavagen 188, S-125 35, Alvsjo, Sweden

[21] Appl. No.: 09/133,320

[22] Filed: Aug. 13, 1998

[51] Int. Cl.[7] .................................................. A61B 19/00
[52] U.S. Cl. .............................. 128/899; 600/30; 600/38; 600/593; 604/99
[58] Field of Search .............................. 600/593, 30, 31, 600/38, 40; 606/151, 157; 604/97, 99, 51, 28; 128/898, 899

[56] References Cited

U.S. PATENT DOCUMENTS

| | | |
|---|---|---|
| 4,592,339 | 6/1986 | Kuzmak et al. . |
| 4,592,355 | 6/1986 | Antebi . |
| 4,696,288 | 9/1987 | Kuzmak et al. . |
| 5,074,868 | 12/1991 | Kuzmak . |
| 5,226,429 | 7/1993 | Kuzmak . |
| 5,509,888 | 4/1996 | Miller ........................................ 600/29 |
| 5,771,903 | 6/1998 | Jakobsson . |

FOREIGN PATENT DOCUMENTS

| | | |
|---|---|---|
| 0611 561 | 8/1994 | European Pat. Off. . |
| WO 94/27504 | 12/1994 | WIPO . |

*Primary Examiner*—Cary O'Connor
*Assistant Examiner*—Pamela Wingood
*Attorney, Agent, or Firm*—Nixon & Vanderhye P.C.

[57] ABSTRACT

A food intake restriction device for surgical application in the abdomen of a patient for forming a stoma opening in the stomach or esophagus of the patient comprises an elongated non-inflatable restriction member, a forming device for forming the elongated restriction member into at least a substantially closed loop around the stomach or the esophagus to define a restriction opening, and a post-operation non-invasive adjustment device for mechanically adjusting the restriction member in the loop to change the size of the restriction opening. The components are of bio-compatible material and are effective for treating morbid obesity over an extended period of time always in a non-invasive manner.

29 Claims, 11 Drawing Sheets

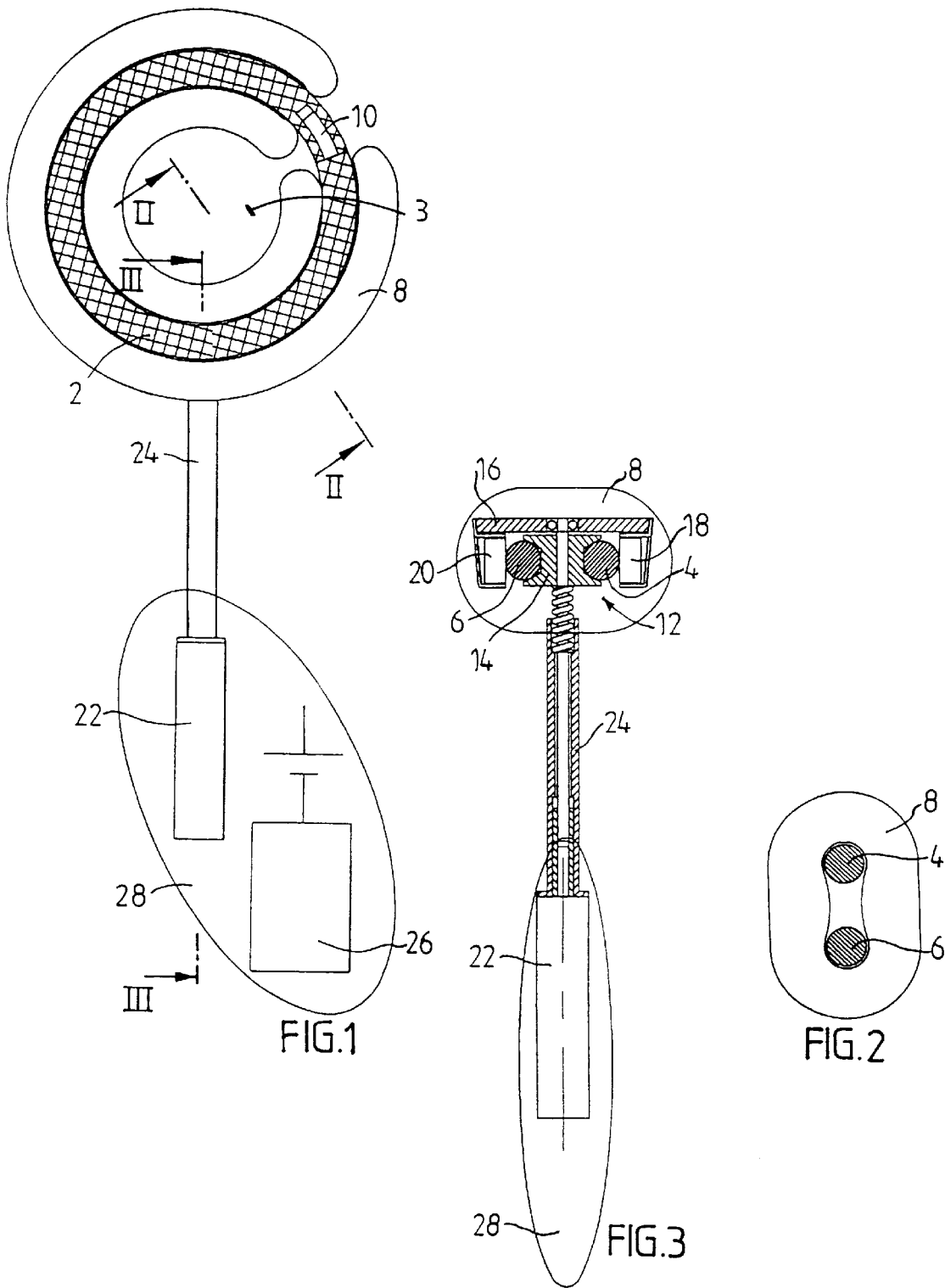

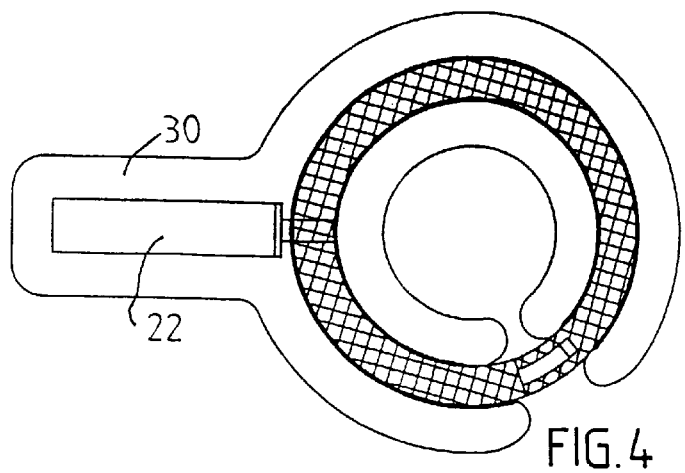
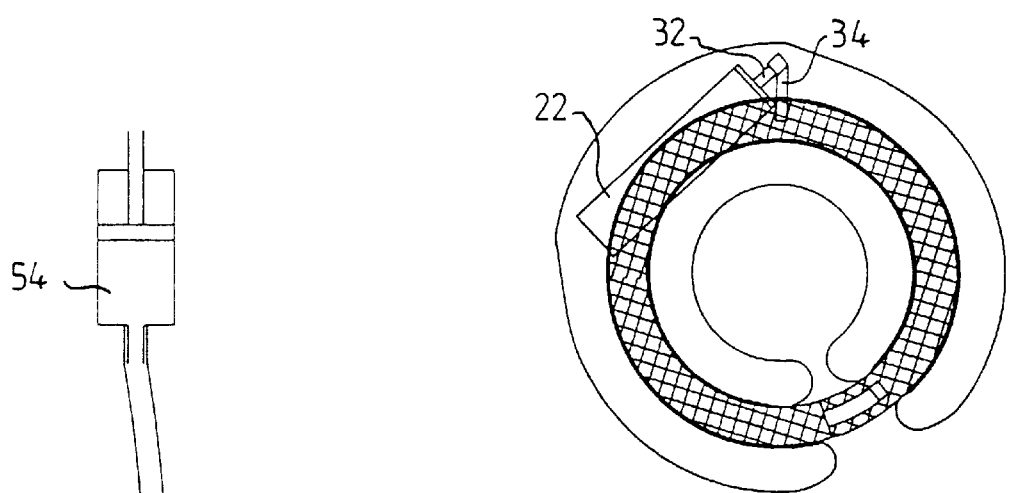
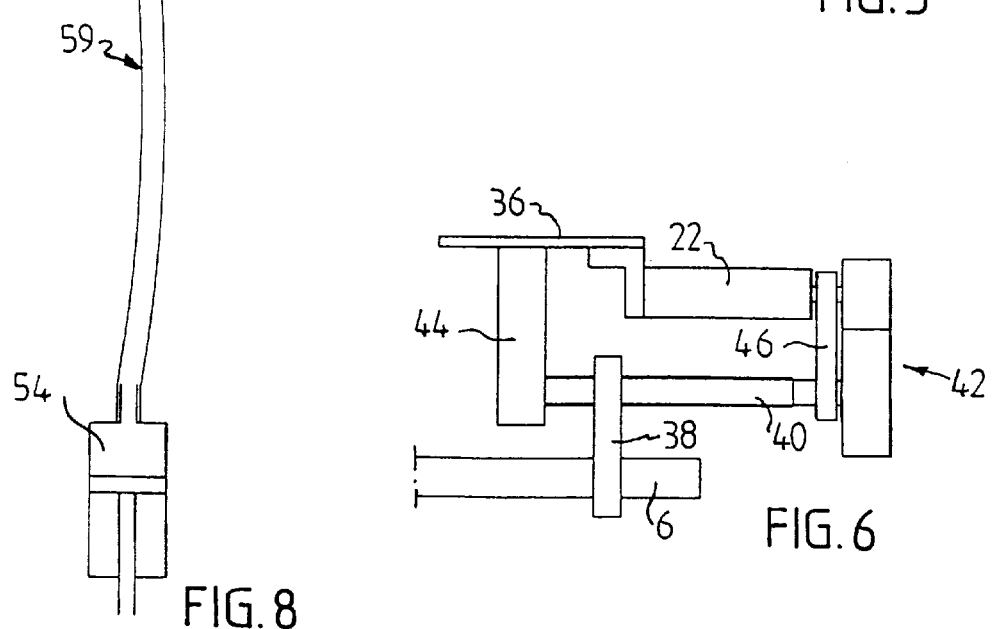

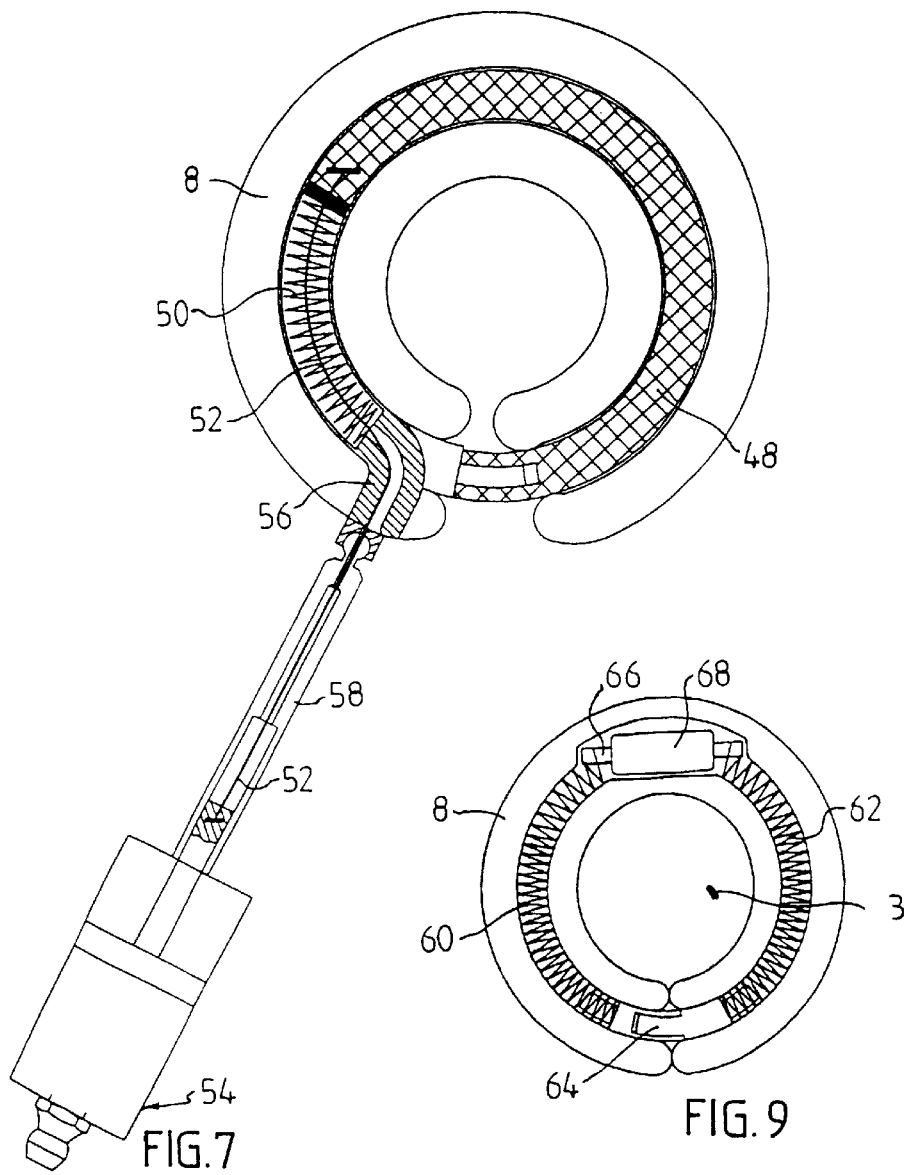
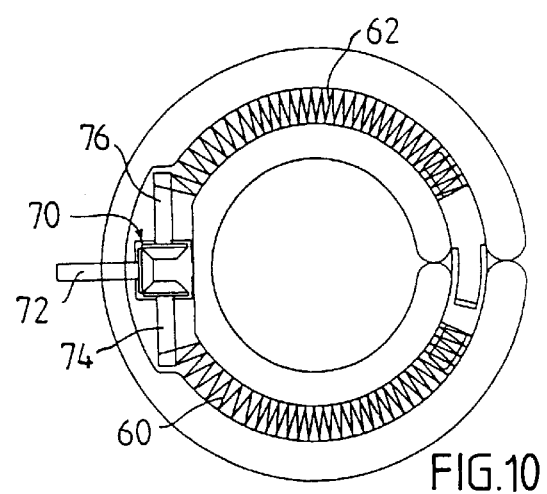
FIG. 7
FIG. 9
FIG. 10

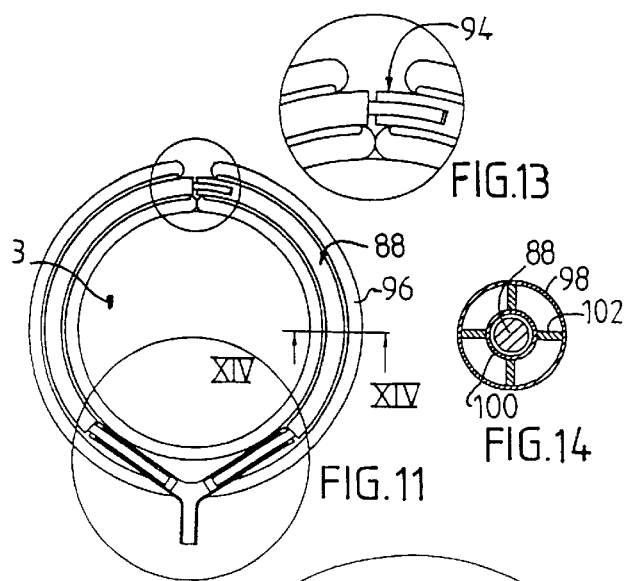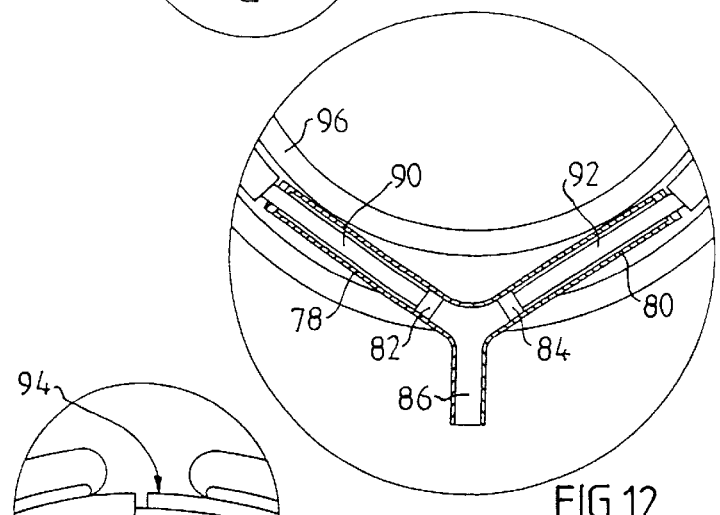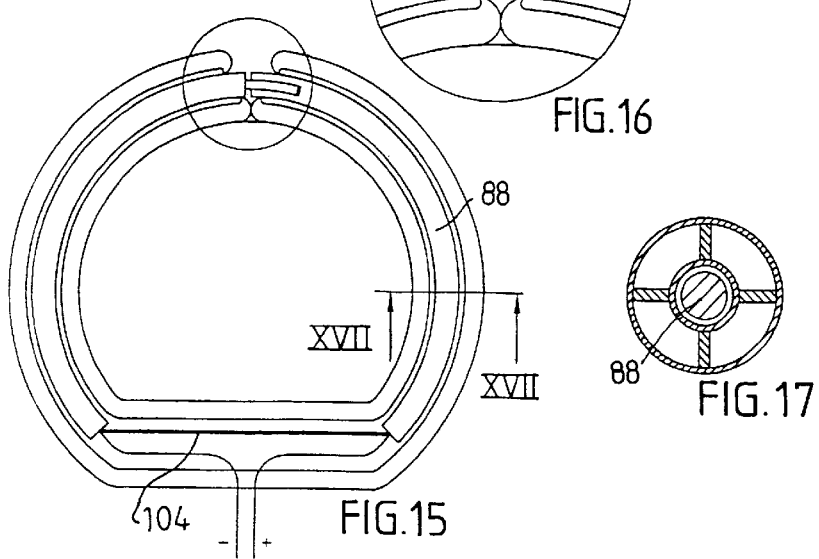

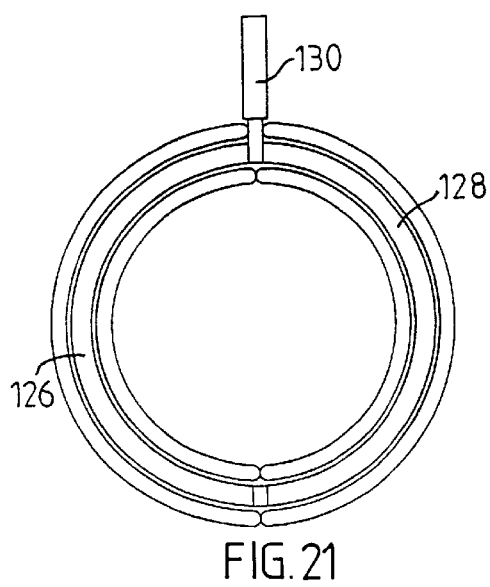
FIG. 21
FIG. 22
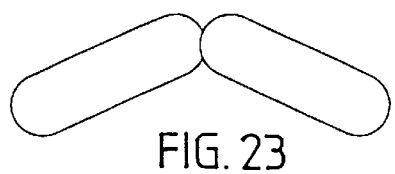
FIG. 23
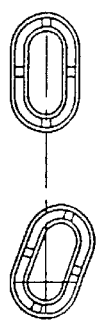
FIG. 27
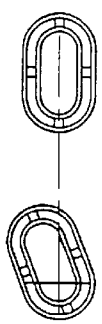
FIG. 26
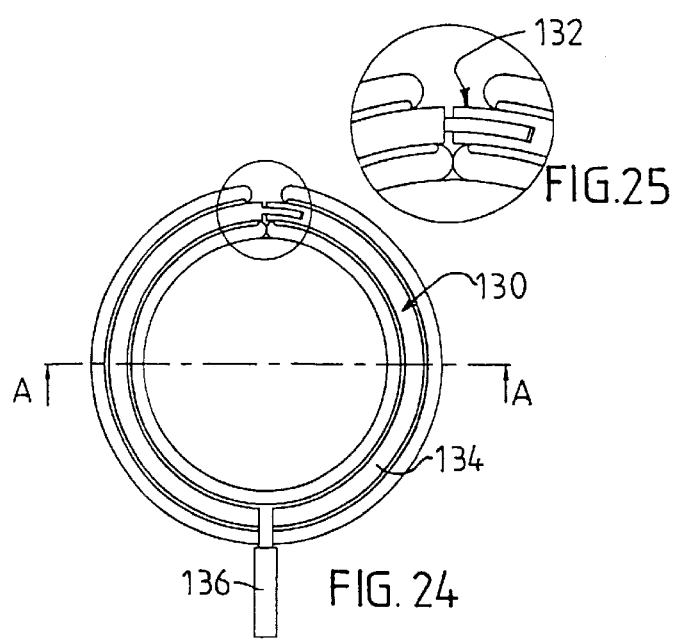
FIG. 25
FIG. 24

NO FLOW

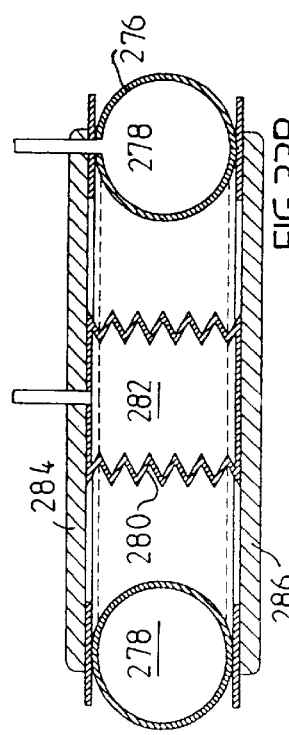
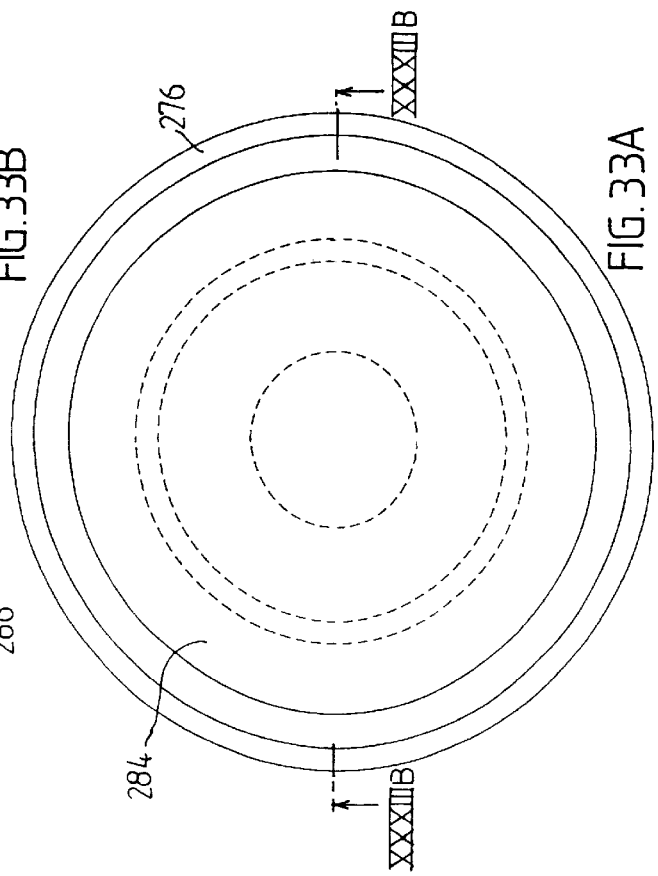
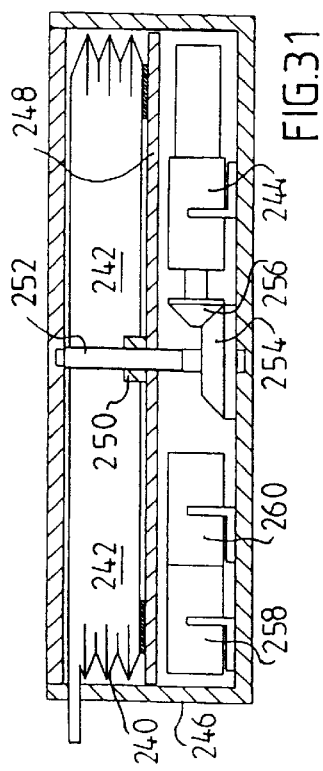
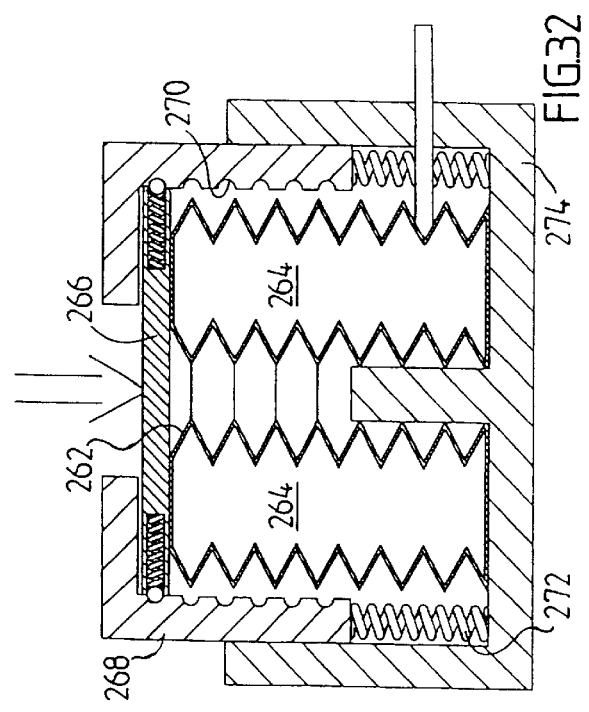

MECHANICAL FOOD INTAKE RESTRICTION DEVICE

BACKGROUND AND SUMMARY OF THE INVENTION

The present invention relates to a mechanical food intake restriction device for the treatment of morbid obesity. More specifically, the invention relates to a mechanical food intake restriction device for surgical application in the abdomen of a patient for forming a stoma opening in the stomach or esophagus of the patient.

Mechanical food intake restriction devices in the form of gastric banding devices, in which a band encircles a portion of the stomach, have been used in surgery for morbid obesity to form a small gastric pouch above the band and a reduced stoma opening in the stomach. Although such a band is applied around the stomach to obtain an optimal stoma opening during surgery, some prior gastric banding devices are provided with an adjustment means enabling a minor post-operation adjustment of the size of the stoma opening. In all such prior art devices such as disclosed in U.S. Pat. No. 4,592,339, European Patent No. 0611561 and International Patent Application WO 94/27504, the adjustment means typically comprises an inflatable cavity in the band and an injection port in fluid connection with the inflatable cavity for adding fluid to or withdrawing fluid from the latter. In practice, the band is made of silicone rubber which is a material approved for implantation and the fluid is a liquid such as an isotonic salt solution.

It has been found, however, that the prior art bands may eventually dislocate downwardly on the stomach and there is an increased risk of stoma stenosis due to a small range of adjustment of the band. It has also been found that the volume of the gastric pouch above the band increases in size up to ten times after an operation. Therefore the pouch volume during surgery needs to be very small, approximately 7 ml. To enable the patient to feed the stomach with sufficient nutrition immediately after an operation considering such a small gastric pouch, the stoma initially needs to be relatively large and later needs to be substantially reduced, as the pouch volume increases. To be able to achieve a significant range of adjustment of the band, the cavity in the band has to be relatively large and is defined by a thin flexible wall, normally made of silicone material. Furthermore, the size of the stoma opening has to be gradually reduced during the first year after surgery as the gastric pouch increases in size. As indicated above, the reduction of the stoma opening using the prior art gastric banding devices is achieved by adding liquid to the cavity of the band via an injection port to expand the band radially inwardly.

A great disadvantage of repeatedly injecting liquid via the injection port is the increased risk of the patient getting an infection in the body area surrounding the injection port. If such an infection occurs the injection port has to be surgically removed from the patient. Moreover, such an infection might be spread along the tube interconnecting the injection port and the band to the stomach causing even more serious complications. Thus, the stomach might be infected where it is in contact with the band, which might result in the band migrating through the wall of the stomach. Also, it is uncomfortable for the patient when the necessary, often many, post-operation adjustments of the stoma opening are carried out using an injection needle penetrating the skin of the patient into the injection port.

Further it may happen that the patient swallows pieces of food too large to pass through the restricted stoma opening. If that occurs the patient has to visit a doctor who can remove the food pieces, if the band design so permits, by withdrawing some liquid from the band to enlarge the stoma opening to allow the food pieces to pass the stoma. Then, the doctor has to add liquid to the band in order to regain the restricted stoma opening. Again, these measures require the use of an injection needle penetrating the skin of the patient, which is uncomfortable for the patient.

Another problem with known adjustable gastric banding devices is that the isotonic salt solution can diffuse from the inflatable cavity of the band through the surrounding band walls of silicone rubber when there is a slight overpressure prevailing in the cavity. There is also a risk some time after the operation of liquid leakage from the injection port, from the tube between the latter and the band, and from the band itself. Most critical is the inflatable balloon cavity.

According to the invention a mechanical food intake restriction device is provided in which the risk of liquid leaking from the device is substantially reduced or eliminated. The invention provides an adjustable mechanical food intake restriction device which does not require the use of an injection needle for accomplishing post-operation adjustments of the stoma opening, and provides an adjustable mechanical food intake restriction device which permits post-operation adjustments that are comfortable for the patient.

In accordance with the invention a mechanical food intake restriction device is provided for surgical application in the abdomen of a patient for forming a stoma opening in the stomach or esophagus of the patient. The device includes an elongated restriction means, a forming means for forming the restriction member into a substantially closed loop around the stomach or esophagus, the loop defining a restriction stoma opening, and a post-operation non-invasive adjustment device for mechanically adjusting the restriction member to change the size of the restriction opening. As a result, there is no liquid directly involved in the elongated restriction member itself for providing inflation thereof, enabling post-operation adjustments of the device of the invention to change the stoma opening of the patient. The adjustment device may be incorporated in the restriction member as well as being controlled by a hydraulic device. The expression "post-operation non-invasive adjustment device" means that the adjustment device is capable of adjusting the restriction member after the operation without the need for invasive measures, such as penetration of the skin for example by injection needles or surgery, or by any other means that penetrate the skin. Though an injection port could be used in embodiments using a hydraulic device, the port preferably would be for enabling a single, once and for all, calibration of the amount of liquid contained by the hydraulic device.

In accordance with a preferred first adjustment principle, the adjustment device adjusts the longitudinal extension of the elongated restriction member in a loop form.

In a preferred embodiment of the invention utilizing the first adjustment principle, the restriction member comprises a main portion and two elongated end portions, and the adjustment device establishes longitudinal relative displacement between the end portions of the restriction member, so that the size of the restriction opening is adjusted. The forming means may comprise any suitable known or conventional device capable of practicing the desired function, such as a spring material forming the elongated restriction member into the loop, so that the restriction opening has a predetermined size, and the adjustment device may adjust the restriction member against the spring action of the spring material. In other words, the restriction member may comprise a spring clip. The spring material may be integrated in the restriction member.

Preferably, the adjustment device comprises a movement transferring member, suitably a drive wheel, in engagement with at least one of the end portions of the restriction member and operable to displace the one end portion relative to the other end portion of the restriction member. The drive wheel may advantageously be in engagement with both of the end portions of the restriction member and be operable to displace the end portions relative to each other. An elongated flexible drive shaft may be operatively connected to the drive wheel, for transferring manual or motor generated power from a location remote from the restriction member. In its simplest embodiment, the drive wheel may comprise a pulley in frictional engagement with the restriction member. As an alternative, a gear rack may be formed on at least one of the end portions of the restriction member and the drive wheel may comprise a gear wheel in mesh with the gear rack. Other suitable known or conventional mechanisms may also or alternatively be used as the adjustment device.

The movement transferring member may alternatively comprise at least one cylinder and a piston, which is movable therein and is connected to one of the end portions of the restriction member, the piston being operable to longitudinally displace the one end portion of the restriction member relative to the other end portion of the restriction member. Alternatively, the movement transferring member may comprise two interconnected cylinders and two pistons in the respective cylinders connected to the end portions, respectively, of the restriction member, the pistons being operable to longitudinally displace the end portions of the restriction member relative to each other. Other known or conventional devices also or alternatively can be used as the movement transferring member.

A motor, which is fixed relative to the main portion of the restriction member and has a rotating drive shaft operatively connected to the movement transferring member, may be positioned relative to the elongated restriction member such that the drive shaft extends transverse thereto. Alternatively, the motor may be positioned relative to the elongated restriction member such that the drive shaft extends substantially tangentially to the loop of the restriction member.

In another embodiment of the invention utilizing the first adjustment principle, the elongated restriction member is longitudinally resilient and the adjustment device comprises a contraction element adapted to longitudinally contract the resilient restriction member. Preferably, the elongated restriction member comprises a substantially nonresilient main portion and an end portion forming an elongated helical spring, which is contractable by the contraction element. The contraction element may suitably comprise an elongated flexible pulling member connected to the main portion of the restriction member and extending through the helical spring to contract the helical spring against an arresting member, which is fixed relative to the main portion of the restriction member. The pulling member may extend in an elongated tube joined at one end thereof to an arresting member, so that a motor remote from the restriction member may be attached to the other end of the elongated tube and pull the pulling member through the tube to contract the helical spring.

In yet another embodiment of the invention utilizing the first adjustment principle, the elongated restriction member comprises an elongated helical spring having a free end, and a body to which the spring is nonrotatably secured at its opposite end. The adjustment device rotates the helical spring in one direction to enlarge the coils of the helical spring to longitudinally contract the spring and to rotate the spring in the opposite direction to reduce the size of the coils of the spring to longitudinally extend the spring. As a preferred alternative, the restriction member comprises a further elongated helical spring having a free end and nonrotatably secured to the body at its opposite end, and the adjustment device comprises a drive shaft having two opposite end portions connected to the springs, respectively, at their free ends, the helical coils forming left and right hand helices, respectively. The adjustment device may alternatively comprise gearing having an input shaft and two opposite aligned output shafts connected to the helical springs, respectively, at their free ends, the input shaft being connected to the output shafts so that the output shafts rotate in the opposite directions upon rotation of the input shaft, the helical coils forming the same helices.

In accordance with a second adjustment principle, the adjustment device mechanically adjusts the restriction member so that at least a portion of a radially innermost circumferential confinement surface formed by the restriction member in the loop of the restriction member is substantially radially displaced in the loop.

In one embodiment of the invention utilizing a second adjustment principle, the restriction member comprises an elongated voltage responsive element forming part of the confinement surface and capable of bending into a bow in response to a voltage applied across the element, the radius of curvature of the bow being adjustable by changing the level of the voltage.

In another embodiment of the invention utilizing the second adjustment principle, the adjustment device changes the diameter of an elastic annular element of the restriction member, which forms the confinement surface. Preferably, the forming means comprises a substantially rigid outer annular element coaxially surrounding the elastic annular element, and the adjustment device comprises a device which pulls the elastic annular element radially outwardly towards the outer annular element to expand the elastic annular element. For example, the pulling device may comprise a plurality of threads secured to the elastic annular element along the circumference thereof and running from the elastic annular element via guide members attached to the outer annular element.

In yet another embodiment of the invention utilizing the second adjustment principle, the forming means comprises a substantially rigid outer annular element, and the restriction member comprises an elongated helical spring extending internally along the outer annular element and contacting the latter. The helical spring forms part of the circumferential confinement surface and has a free end. The restriction member further comprises a body to which the spring is nonrotatably secured at its opposite end. The adjustment device is adapted to rotate the helical spring in one direction to enlarge the coils of the spring to contract the circumferential confinement surface and to rotate the spring in the opposite direction to reduce the size of the coils of the spring to expand the circumferential confinement surface. As an alternative, which is preferred, the restriction member comprises two elongated helical springs forming part of the circumferential confinement surface and connected to the body of the restriction member. The adjustment device rotates each spring in one direction to enlarge the coils of the spring to contract the circumferential confinement surface and to rotate the spring in the opposite direction to reduce the size of the coils of the spring to expand the circumferential confinement surface.

In accordance with a third adjustment principle, the restriction member comprises at least two separate elements, at least one of which is pivoted so that it may turn in a plane in which the loop of the restriction member extends, and the adjustment device turns the pivoted element to change the size of the restriction opening. Preferably, the restriction member comprises a plurality of separate pivoted elements disposed in series, each pivoted element being turnable in the plane, and the adjustment device turns all of the pivoted elements to change the size of the restriction opening. For example, the pivoted elements may comprise lamellae arranged like the conventional adjustable aperture mechanism of a camera.

In accordance with a fourth adjustment principle, the adjustment device folds at least two foldable frame elements of the restriction member towards each other. Preferably, the foldable frame elements comprise two substantially semi-circular frame elements which are hinged together so that the semi-circular elements are swingable relative to each other from a fully open state in which they form a circle to a fully folded state in which they form a semi-circle.

In accordance with a fifth adjustment principle, the adjustment device turns the restriction member around a longitudinal extension thereof, the elongated restriction member being elastic and varying in thickness as seen in a cross-section therethrough. Suitably, the elongated restriction member comprises an elastic belt.

In all of the above-described embodiments of the invention the adjustment device is conveniently operated by any suitable motor, preferably an electric motor, which may be fixed directly to or be placed in association with the restriction member, or alternatively may be located remote from the restriction member, advantageously in the abdomen or subcutaneously. In the latter alternative the motor is advantageously connected to the adjustment device by a flexible power transmission conduit to permit suitable positioning of the motor in the abdomen of the patient. The motor may be manually activatable, for example by an implanted switch.

In some of the above described embodiments of the invention, however, the adjustment device may conveniently be operable by a hydraulic device, which preferably is manually activatable. The hydraulic device may advantageously include hydraulic servo means to facilitate manual activation. As an alternative, the hydraulic device may be powered by an electric motor, which may be manually activatable or controlled by a remote control device. The components of such a hydraulic device may be placed in association with the restriction member and/or be located at a suitable place in the abdomen or subcutaneously.

More specifically, a reservoir may be provided containing a predetermined amount of fluid for supplying the hydraulic device with hydraulic fluid. The reservoir defines a chamber for the predetermined amount of fluid and the hydraulic device changes the size of the chamber. The hydraulic device may comprise first and second wall portions of the reservoir, which are displaceable relative to each other to change the size of the chamber of the reservoir. The first and second wall portions of the reservoir may be displaceable relative to each other by manual manipulation thereof, preferably to permit manual pushing, pulling or rotation of any of the wall portions in one direction. Alternatively, the wall portions may be displaceable relative to each other by magnetic means (such as a permanent magnet and magnetic material reed switch, or other known or conventional magnetic devices), hydraulic means, or electric control means such as an electric motor. The magnetic means, hydraulic means, or electrical control means may all be activated by manual manipulation, preferably using a subcutaneously located manually manipulatable device. This control may be indirect, for example via a switch.

The hydraulic device may be adapted to operate the adjustment device with fluid from the reservoir in response to a predetermined first displacement of the first wall portion of the reservoir relative to the second wall portion of the reservoir, to increase the size of the restriction opening, and to operate the adjustment device with fluid from the reservoir in response to a predetermined second displacement of the first wall portion of the reservoir relative to the second wall portion of the reservoir, to decrease the size of the restriction opening. In this embodiment, no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

As an alternative, the hydraulic device may comprise an activatable pump for pumping fluid between the reservoir and the adjustment device. The pump may pump fluid both to and away from the adjustment device, or hydraulic means controlling the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated manually, mechanically, electrically, magnetically, or hydraulically. Any kind of motor could of course be used for all the different operations as well as wireless remote solutions. The pump may comprise a first activation member for activating the pump to pump fluid from the reservoir to the adjustment device, and a second activation member for activating the pump to pump fluid from the adjustment device to the reservoir. The activation members may be operable by manual manipulation, preferably to permit manual pushing, pulling, or rotating thereof in one direction. Suitably, at least one of the activation members operates when subjected to an external pressure exceeding a predetermined magnitude.

Alternatively, at least one of the first and second activating members may be operable by magnetic means, hydraulic means, or electric control means such as an electric motor. The magnetic means, hydraulic means, or electrical control means may all be activated by manual manipulating means preferably located subcutaneously. This activation may be indirect, for example via a switch.

Advantageously, especially when manual manipulation means are used, a servo means system could be used. With servo means less force is needed for controlling the adjustment device. Hydraulic means is preferably used with servo means. One example is a closed system that controls another closed system in which the hydraulic means of the adjustment device is incorporated. Minor changes in the amount of fluid in a reservoir of the first system could then lead to major changes in the amount of fluid in a reservoir in the second system. In consequence, the change of volume in the reservoir of the second system affects the hydraulic means of the adjustment device, which is incorporated in the second closed system. The great advantage of this servo system is that the larger volume system could be placed inside the abdomen where there is more space and it still would be possible to use manual manipulation means of the smaller system subcutaneously. The servo reservoir could control the reservoir of the larger volume. The servo reservoir could be controlled directly or indirectly by a fluid supply means. The fluid supply means may be a small reservoir, which may be placed subcutaneously and may be activated by manual manipulation means controlling the servo reservoir.

Preferably, the servo means comprises hydraulic means and a servo reservoir and eventually a fluid supply reservoir. Both reservoirs define a chamber containing servo fluid, and the hydraulic device comprises first and second wall portions of the servo reservoir, which are displaceable relative to each other to change the size of the chamber of the servo reservoir. The hydraulic device may control the adjustment device indirectly, e.g. via an increased amount of fluid in the servo reservoir, in response to a predetermined first displacement of the first wall portion of any of the reservoirs relative to the second wall portion of the servo reservoir to decrease the size of the restriction opening, and to control the adjustment device in response to a second displacement of the first wall portion of any reservoir relative to the second wall portion, to indirectly increase the size of the restriction opening. The wall portions of the servo reservoirs may be designed to be displaceable relative to each other by manual manipulation thereof or be displaceable relative to each other by manually pushing, pulling or rotating any of the wall portions of the servo reservoir in one direction. Alternatively, the wall portions of the servo reservoir or fluid supply and reservoir may be displaceable relative to each other by magnetic means, hydraulic means or electric control means including an electric motor.

The magnetic means, hydraulic means, or electrical control means may all be activated by manually manipulated means preferably located subcutaneously. This control may be indirect for example via a switch.

Even in the broadest embodiment of the invention the adjustment device may comprise a servo means. The servo means may comprise a hydraulic operation means, an electric control means, a magnetic means, mechanical means or a manual manipulating means. The hydraulic operation means, electric control means, mechanical means or magnetic means may be activated by manual manipulating means. Using a servo system will save the use of force when adjusting the adjustment device which may be of importance in many applications, for example when a battery cannot put out enough current although the total energy in the battery is more than enough to power the system.

All solutions may be controlled by a wireless remote control means. Preferably, the remote control means comprises a motor for operating the adjustment device and an energizer for providing energy, and a signal receiving means comprises a control unit for powering the motor with energy provided by an energizer unit in response to a signal received from a signal transmitting means. Any known or to be developed remote control system may be used for this purpose.

The energizer unit may comprise a power supply that could be rechargeable, and the control unit powers the motor with energy from the power supply. Preferably, the power supply is an electric power supply such as a battery, and the motor is an electrical motor. In this case, the battery also continuously powers the circuitry of the signal receiving means between the adjustment operations, in order to keep the signal receiving means prepared for receiving signals transmitted from the transmitting means.

The motor may be any type of motor, such as pneumatic, hydraulic or electric motor and the energizer unit may be adapted to power the motor with pressured gas or liquid, or electrical energy, depending on the type of motor. Of course, in case the motor is an electrical motor, it may power pneumatic or hydraulic equipment.

Advantageously, the signal transmitting means transmits electromagnetic wave signals and the energizer draws radiant energy from the electromagnetic wave signals as they are transmitted to the signal receiving means and transfers the radiant energy into electric energy for powering an electric motor. The energizer unit may comprise a rechargeable electric power supply, such as a capacitor for storing the electric energy and the control unit may be in the rechargeable electric power supply in response to signals received from the signal transmitting means.

The energizer unit may draw radiant energy from the electromagnetic wave signals received by the signal receiving means and as they are transmitted, and transfer the radiant energy into electric energy for powering the motor. This is only practicable, however, if the adjustment device is of a type that requires little power for its operation, because in practice the electromagnetic wave signals transmitted in this connection often are of low power. Advantageously in an initial charging step the rechargeable power supply can be charged during a period of time without powering the electric motor. In a following step, when the power supply has been charged with sufficient energy, the control unit powers the electric motor with energy from the charged power supply to operate the adjustment device, direct or indirect, so that a desired change of the patient's stoma opening is achieved. If the capacity of the power supply is insufficient to achieve the necessary adjustment in one single operating step, the above steps may be repeated until the desired adjustment is achieved. Both these solutions are particularly simple and do not require any recurrent invasive measures for exchanging empty power supplies, such as batteries, that are required in an earlier described solution.

As an alternative, the energizer unit may comprise a battery, and/or an electrically operable switch to connect the battery to the signal receiving means in an on mode when the switch is powered and to keep the battery disconnected from the signal receiving means in a standby mode when the switch is unpowered, and a rechargeable electric power supply for powering the switch. The control unit may power the electric motor with energy from the battery in response to signals received from the signal transmitting means, when the switch is in its on mode. Suitably, the energizer unit may transfer the radiant energy into a current for charging the rechargeable electric power supply such as a capacitor. This solution is suited for adjustment devices of the type that require relatively high power for operation and has the advantage that the electronic circuitry of the signal receiving means does not have to be powered by the battery between adjustment operations, as described above in connection with the embodiment in which only a battery is used for powering the motor in response to signals to the signal receiving means. As a result, the lifetime of the battery can be substantially prolonged.

The energizer unit may comprise a coil connected to the signal receiving means for inducing an alternating current as electromagnetic wave signals are transmitted through said coil to the signal receiving means and a rectifier for rectifying the alternating current. The rectified current is used for charging the rechargeable power source, for instance a capacitor.

As should be realized by a skilled person, in many of the above-described embodiments of the invention the adjustment device may be operated by a control device, or manually manipulated device implanted under the skin of the patient, such as a pump, an electrical switch, or a mechanical movement transferring device. In the manual embodiment it is not necessary to use a motor for operating the adjustment device.

In embodiments including hydraulic transmission means, an injection port connected to the hydraulic means may be provided for enabling, normally single, once-and-for-all, calibration of the amount of fluid in the hydraulic system.

The invention also comprises a method comprising (a) surgically implanting in the abdomen of a patient with morbid obesity a mechanical food intake restriction device which forms a stoma opening in the stomach or esophagus, by forming an elongated non-inflatable restriction member (e.g. of bio-compatible material, or covered by bio-compatible material) into at least a substantially closed loop around the stomach or the esophagus of the patient, the loop defining a restriction opening; and then (b) when necessary for the patient's health or desired progress, in a non-invasive procedure mechanically adjusting the restriction member to change the size of the restriction opening. In this method, (a) may be practiced by implanting a restriction member comprising a main portion and two elongated end portions; and (b) may be practiced by establishing a longitudinal relative displacement between the end portions of the restriction member so that the size of the restriction opening is adjusted.

In the method, (a) may be practiced using laparoscopic techniques, such as shown generally in copending application Ser. No. 09/106,142 filed Jun. 29, 1998, the disclosure of which is incorporated by reference herein. For example, the method may be practiced by: (i) inflating the patient's abdomen with gas by penetration of the patient's skin, (ii) introducing at least one (e.g. two) laparoscopic trocars into the abdomen to introduce the elongated restriction member and one or more medical instruments, and then (iii) forming the elongated restriction member into the at least substantially closed loop.

Also, in practicing the method of the invention, (a) may be practiced by implanting a restriction member having a radially innermost circumferential confinement surface formed in the loop; and wherein (b) is practiced by causing at least a portion of the confinement surface to be radially displaced in the loop.

The invention may also comprise a surgical method for implanting a non-inflatable food restriction device for forming a stoma opening in the stomach or esophagus comprising: (a) Insufflating the abdomen of a patient to form a pneumoperitoneum. (b) Introducing at least one laparoscopic trocar into the abdomen. (c) Using a dissecting tool inserted through the laparoscopic trocar, dissecting the region of the esophagus or stomach preferably above the bursa omentalis. (d) Introducing the non-inflatable food restriction device in the abdomen and applying the device in at least a substantially closed loop around the stomach or esophagus. And, (e) post-operatively adjusting the restriction opening in a non-invasive procedure.

It is the primary object of the present invention to provide an advantageous yet relatively simple assembly and method for treating morbid obesity in a substantially non-invasive manner after initial surgical implantation of a non-inflatable restriction member. This and other objects will become clear from the detailed description and from the appended claims.

BRIEF DESCRIPTION OF THE DRAWINGS

FIG. 1 is a schematic sectional view of a preferred first embodiment of one exemplary device in accordance with the invention;

FIGS. 2 and 3 are cross-sectional views taken along the lines II—II and III—III, respectively, of FIG. 1;

FIGS. 4 and 5 schematically show two alternative designs of the embodiment of FIG. 1;

FIG. 6 schematically illustrates a motor arrangement for the design according to FIG. 5;

FIG. 7 is a schematic sectional view of a second embodiment of the device in accordance with the invention;

FIG. 8 schematically illustrates a hydraulic transmission conduit for the embodiment of FIG. 7;

FIG. 9 is a schematic sectional view of a third embodiment of the device in accordance with the invention;

FIG. 10 is a modification of the embodiment of FIG. 9;

FIG. 11 is a schematic view of a fourth embodiment of the device in accordance with the invention;

FIGS. 12 and 13 are enlarged details of the embodiment of FIG. 11;

FIG. 14 is a cross-section along the line XIV—XIV of FIG. 11;

FIG. 15 is a schematic view of a fifth embodiment of the device in accordance with the invention;

FIG. 16 is an enlarged detail of FIG. 15;

FIG. 17 is a cross-section along the line XVII—XVII of FIG. 15;

FIGS. 18 to 21 are schematic sectional views of a sixth, seventh, eighth and ninth embodiments, respectively, of a device in accordance with the invention;

FIGS. 22 and 23 illustrate a fully open and a reduced restriction opening, respectively, of the embodiment of FIG. 21;

FIG. 24 is a schematic view of a tenth embodiment of the device in accordance with the invention;

FIG. 25 is an enlarged detail of the embodiment of FIG. 24;

FIGS. 26 and 27 illustrate a fully open and a reduced restriction opening, respectively, of the embodiment of FIG. 24;

FIG. 31 is a cross-sectional view of a reservoir having a variable volume controlled by a remote control motor, in accordance with a particular embodiment of the principal embodiment shown in FIG. 29B or 30B;

FIG. 32 is a cross-sectional view of a reservoir having a variable volume adjustable by manual manipulation, in accordance with a particular embodiment of the principal embodiment shown in FIG. 29B or 29D;

FIG. 33A is a front view of a hydraulic, pneumatic or mechanical servo system in accordance with a particular embodiment of the principal embodiment shown in FIG. 29D;

FIG. 33B is a cross-sectional view taken along line VB—VB of FIG. 33A.

DETAILED DESCRIPTION OF THE DRAWINGS

Figure 18:
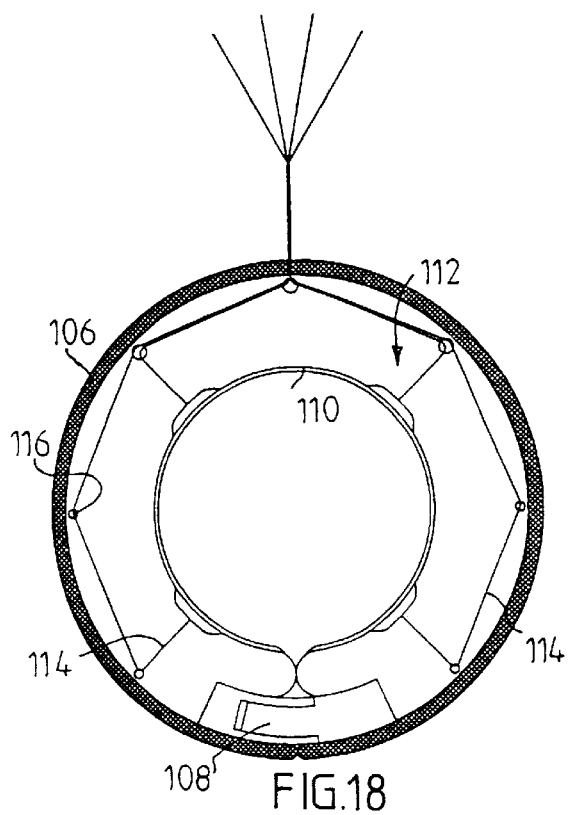

Referring to the drawing figures, like reference numerals designate identical or corresponding elements throughout the several figures.

FIGS. 1–3 show a preferred embodiment of the device of the invention comprising a restriction member in the form of a substantially circular resilient core 2 with two overlapping end portions 4,6. The core 2 defines a substantially circular restriction opening 3 and is enclosed in an elastic soft hose 8 except at a releasable and lockable joint 10 of the core 2, which when released enables application of the core 2 with its hose 8 around the esophagus or the stomach of a patient. The materials of all of these elements are bio-compatible so that the patient's body will not reject them. A post-operation mechanical adjustment device 12 which mechanically adjusts the longitudinal extension of the core 2 to change the size of the restriction opening 3 comprises, in this exemplary embodiment, a drive wheel 14 in frictional engagement with the overlapping end portions 4,6 of the core 2. The drive wheel 14 is journalled on a holder 16 placed in the hose 8 and provided with two counter pressure rollers 18,20 pressing the respective end portions 4, 6 of the core 2 against the drive wheel 14 to increase the frictional engagement therebetween. An electric motor 22 is connected to the drive wheel 14 via a long flexible drive shaft 24 and is molded together with a remote controlled power supply unit 26 in a body 28 of silicone rubber. The length of the flexible drive shaft 34 is selected so that the body 28 can be placed in a desired position in the abdomen of the patient.

If some time after the operation the patient needs an adjustment of the restriction opening 3 of the core 2, the power supply unit 26 is controlled to power the electric motor 22 either to turn the drive wheel 14 in one direction to reduce the diameter of the core 2 or to turn the drive wheel 14 in the opposite direction to increase the diameter of the core 2.

Alternatively, a rack gear may be formed on one of the end portions 4,6 of the core 2 and the drive wheel 14 may be replaced by a drive gear wheel connected to the other end portion of the core 2 and in mesh with the rack gear.

FIG. 4 shows an embodiment of the invention which is identical to the embodiment of FIGS. 1–3, except that the motor 22 is encapsulated in a lateral protrusion 30 of the hose 8 so that it is fixed to the core 2 and has a short drive shaft 32 onto which the drive wheel 14 is mounted, the motor 22 being positioned relative to the circular core 2 such that the drive shaft 32 extends radially thereto.

FIG. 5 shows an embodiment of the invention which likewise is identical to the embodiment of FIGS. 1–3, except that the motor 22 is encapsulated in the hose 8 so that it is fixed to the core 2 and has a short drive shaft 32, the motor 22 being positioned relative to the core 2 so that the drive shaft 32 extends substantially tangentially to the circular core 2. There is an angular gearing 34 connecting the drive shaft 32 to the drive wheel 14.

FIG. 6 shows a suitable arrangement for the motor 22 in the embodiment of FIG. 5, comprising a first clamping member 36 secured to one end portion 4 of the core 2 and a second clamping member 38 secured to the other end portion 6 of the core 2. The motor 22 is secured to the first clamping member 36 and is operatively connected to a worm 40 via a gear transmission 42. The worm 40 is journalled at its opposite ends on holders 44 and 46, which are rigidly secured to the clamping member 36 and the motor 22, respectively. The second clamping member 38 has a pinion in mesh with the worm 40. When the motor 22 is powered the worm 40 rotates and will thereby pull the end portion 6 of the core 2 in one or the opposite longitudinal direction, so that the diameter of the substantially circular core 2 is either increased or decreased.

FIG. 7 shows an embodiment of the invention in which the restriction member comprises an elongated core 48 and a helical spring 50. A spring contraction device, illustrated in the form of a flexible pulling member 52, i. e. a string, wire, or cable, is connected to the core 48 at one end thereof and extends through the helical spring 50. A hydraulic motor in the form of a cylinder/piston unit 54 pulls the flexible pulling member 52 to contract the helical spring 50 against an arresting member 56, which is fixed relative to the core 48. A tube 58 hinged to the arresting member 56 extends between the cylinder/piston unit 54 and the arresting member 56, the flexible pulling member 52 running through the tube 58 and being connected to the piston of the cylinder/piston unit 54. FIG. 8 shows a similar embodiment in which a hydraulic transmission conduit 59 is provided between two piston-cylinder assemblies 54, for use as the hydraulic motor/device in FIG. 7.

FIG. 9 shows an embodiment of the invention in which the restriction member comprises two elongated helical springs 60 and 62 having free ends, and a body 64 to which the springs 60,62 are nonrotatably secured at their opposite ends. The body 64 comprises two separate parts secured to opposite end portions of the enclosing elastic hose 8 and is designed with a releasable and lockable joint between the separate parts. An adjustment device in the form of a drive shaft 66 has two opposite end portions connected to the helical springs 60, 62, respectively, at their free ends. The coils of the springs 60, 62 form left and right hand helices, respectively. A motor 68 rotates the drive shaft 66 in one direction to enlarge the coils of the helical springs 60, 62, to longitudinally contract the springs 60, 62, and rotates the drive shaft 66 in the opposite direction to reduce the size of the coils of the springs 60, 62 to longitudinally extend the springs 60, 62. Thus, the elongated helical springs 60, 62 define a restriction opening 3, the size of which is increased when the springs 60, 62 are extended and decreased when the springs 60,62 are contracted.

FIG. 10 shows an embodiment according to the invention which is identical to the embodiment of FIG. 9, except that the adjustment device comprises a gearing having an input shaft 72 and two opposite aligned output shafts 74 and 76 connected to the helical springs 60 and 62, respectively, at their free ends. The input shaft 72 is connected to the output shafts 74,76 such that they rotate at opposite directions upon rotation of the input shaft 72. The coils of the spring 60, 62 form the same helices.

FIGS. 11–14 shows an embodiment of the device of the invention in which a hydraulic motor comprises two interconnected cylinders 78 and 80 and two pistons 82 and 84 in the respective cylinders 78,80. The cylinders 78,80 have a common fluid supply inlet member 86, which together with the cylinders 78,80 takes the shape of a Y-pipe. The restriction member comprises an elongated resilient arcuate core 88. The adjustment device comprises two bars 90 and 92 secured to opposite ends of the core 88 and connected to the pistons 82 and 84, respectively. The core 88 defines a restriction opening 3 and is provided with a releasable and lockable joint 94 (FIG. 13) to permit application of the device around the esophagus or stomach of a human patient. The core 88 and the cylinders 90,92 are enclosed by a soft elastic hose 96 except at the joint 94 and the inlet member 86. The hose 96 has an outer tubular wall 98 and a central coaxial inner tubular wall 100, which is fixed to the outer wall 98 by spoke members 102 (FIG. 14). The core 88 is loosely fit in the inner tubular wall 100. By supplying fluid to or withdrawing fluid from the inlet 86 the pistons 82 and 84 will move towards or from each other, so that the restriction opening 3 defined by the core 88 is changed by the longitudinal displacement of the bars 90,92.

FIGS. 15–17 show an embodiment of the invention which is identical to the embodiment of FIGS. 11–14, except that the adjustment device comprises an elongated voltage responsive element 104 secured to the opposite ends of the core 88, so that the core 88 and the element 104 form the restriction member. The element 104 is capable of bending inwardly into a bow in response to a voltage applied across the element 104. The radius of curvature of the bow is adjustable by changing the level of the voltage applied to element 104.

FIG. 18 shows an embodiment of the device of the invention comprising a loop forming device in the form of a substantially rigid outer circular element 106 with a releasable and lockable joint 108 to enable application of the device around the esophagus or stomach of a patient. In this embodiment the restriction member comprises an elastic inner circular element 110 formed by the innermost wall portion of an elastic hose 112 extending along the outer element 106. The inner circular element 110 is disposed concentrically within the outer circular element 106. The adjustment device comprises a plurality of threads 114 secured to the elastic inner element 110 along the circumference thereof and running from the inner element 110 via guide members 116 attached to the outer element 106. By pulling all the threads 114 the inner elastic element 110 is pulled under expansion radially outwardly towards the outer element 106.

Figure 19:
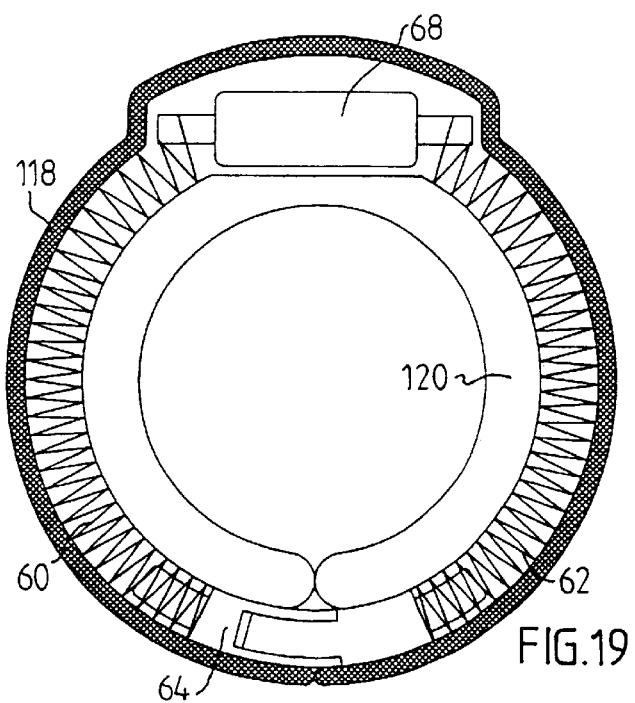

FIG. 19 shows an embodiment which is identical to the embodiment of FIG. 9, except that it comprises a loop forming device in the form of a substantially rigid outer circular element 118 supporting the helical springs 60,62, and a soft elastic inner wall 120 extending along the springs 60,62. When the motor 68 rotates the helical springs 60, 62 in a direction that enlarges the coils of the springs 60,62, the coils are forced by the rigid outer element 118 to expand radially inwardly thereby reducing the size of the restriction opening 3 formed by the circumferential confinement surface of the restriction member (springs 60,62 and body 64).

Figure 20:
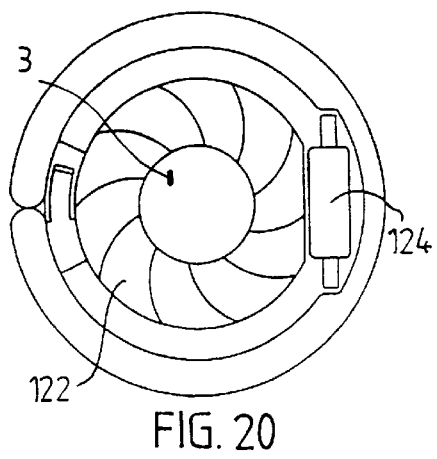

FIG. 20 shows an embodiment of the invention in which a restriction member comprises a plurality of arcuate lamellae 122 arranged like the conventional adjustable aperture mechanism of a camera. The adjustment device, not shown, is conventional and is operated by a motor 124 to adjust the lamellae 122 to change the size of the restriction opening 3 defined by the lamellae 122.

FIGS. 21–23 show an embodiment of the invention in which a restriction member comprises two semi-circular elements 126 and 128 which are hinged together such that the semi-circular elements 126,128 are swingable relative to each other between a fully open state in which they substantially form a circle, illustrated in FIG. 22 and an angular state, in which the size of the restriction opening defined by the semi-circular elements 126,128 is reduced, illustrated in FIG. 23. The adjustment device, not shown, is conventional and is operated by a motor 130 to swing the semi-circular elements 126,128 relative to each other.

FIGS. 24–27 show an embodiment of the invention in which the restriction member comprises an elastic belt 130 forming a circle and having a substantially oval cross-section. The restriction member 130 is provided with a releasable and lockable joint 132. An elastic double walled hose 134 encloses the belt 130 except at the joint 132. The adjustment device, not shown, is conventional and is operated by a motor 136, to turn the belt 130 around the longitudinal extension thereof between a fully open state, in which the inner broader side of the belt 130 forms a substantially cylindrical surface, illustrated in FIG. 26, and a reduced open state, in which the inner broader side of the belt 130 forms a substantially conical surface, illustrated in FIG. 27.

Figure 28:
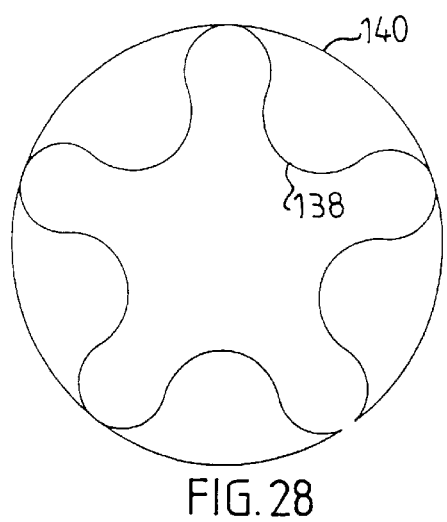
FIG. 28 schematically illustrates a cushion arrangement for protecting the esophagus and the stomach.

FIG. 28 schematically illustrates a cushion arrangement for protecting the esophagus and the stomach of a patient, comprising a plurality of cushions 138 disposed in series along a substantially circular holding member 140. This cushion arrangement is meant to protect the esophagus or stomach of a patient and may be utilized in any of the above described embodiments of the invention.

Figure 29A:
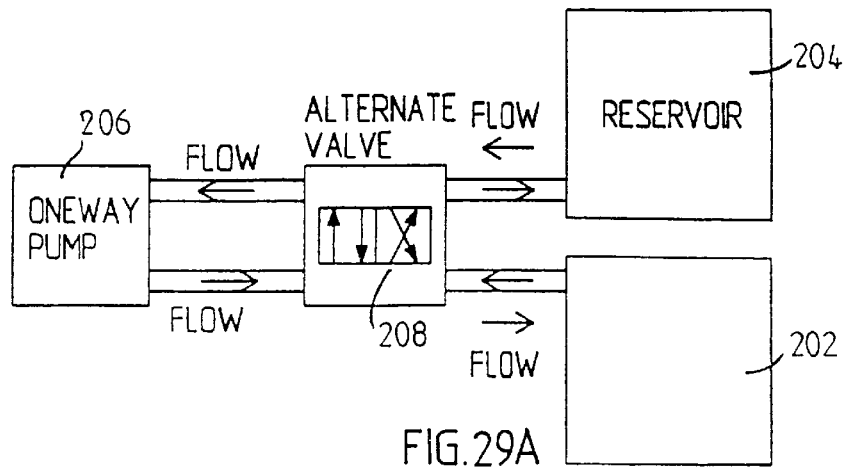
FIGS. 29A–D is a block diagram of four different principal embodiments of the invention.
Figure 29B:
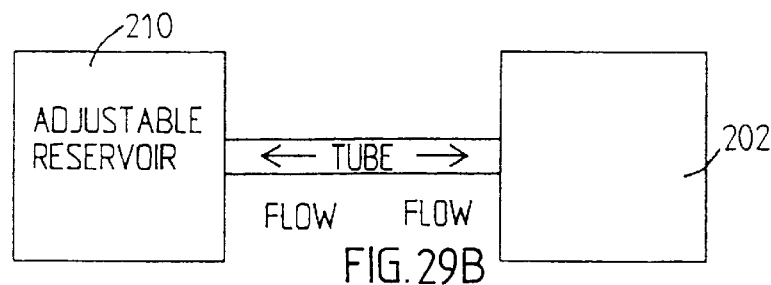
Figure 29C:
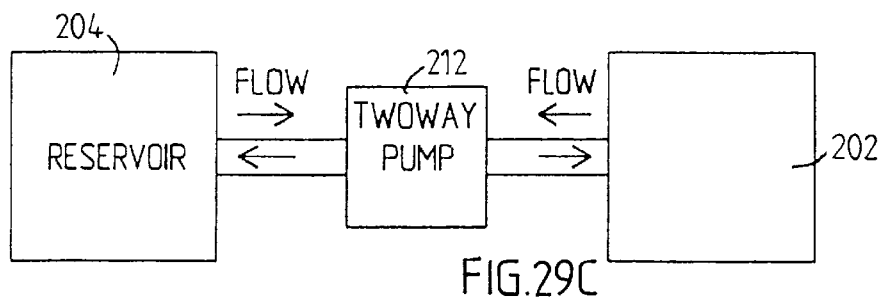

FIGS. 29A–D provide a block diagram of four different hydraulic transmission configurations. FIG. 29A shows an adjustment device 202 of the restriction member, a separate reservoir 204, a one way pump 206, and an alternate valve 208. FIG. 29B shows the adjustment device 202 and an adjustable reservoir 210. FIG. 29C shows the adjustment device 202, a two way pump 212 and the reservoir 204. FIG. 30D shows a servo system with a first closed system controlling a second system. The servo system comprises the adjustable reservoir 210 and a passive adjustable reservoir 214. Any of the reservoirs can be the active reservoir, either the servo reservoir 210 or the fluid supply reservoir 214. The reservoir 214 controls a larger adjustable reservoir 216 which is used for the operation of the adjustment device 202 for changing the restriction opening of the restriction member.

Figure 30A:
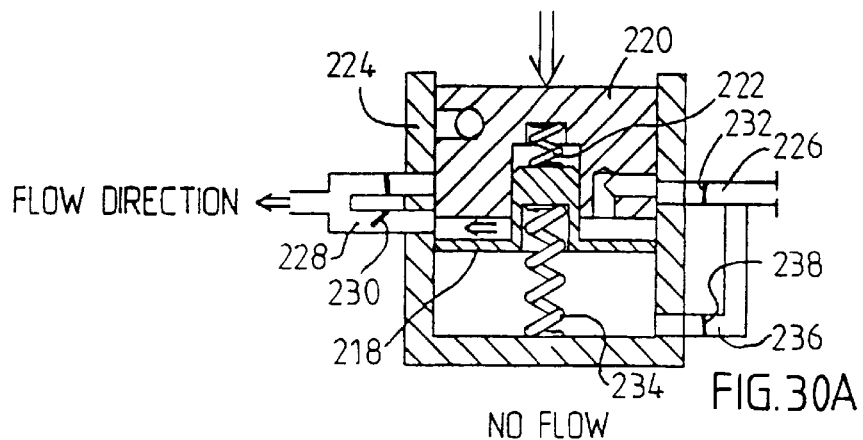
FIGS. 30A–D are cross-sectional views of a pump mechanism according to FIG. 29C, which pumps fluid in opposite directions by mechanically pushing a wall portion in only one direction.
Figure 30B:
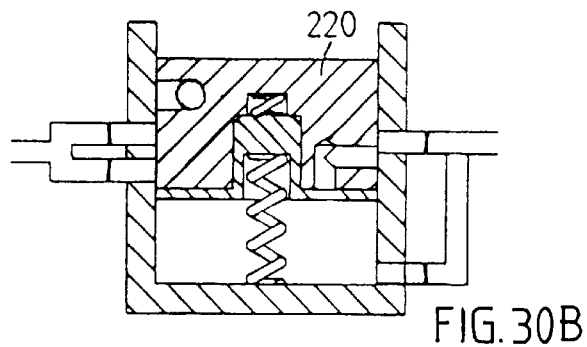
Figure 30C:
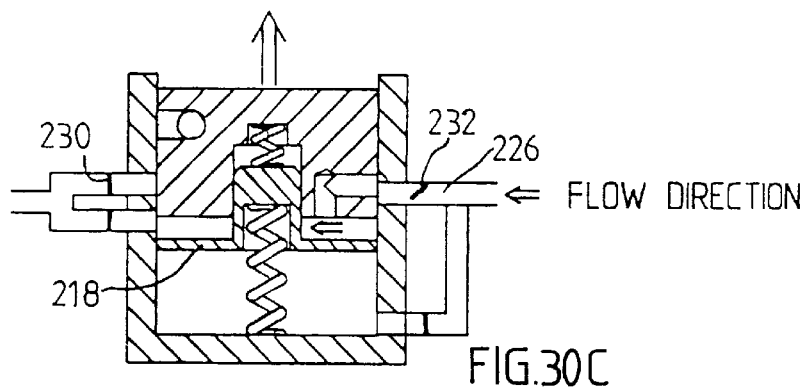

FIGS. 30A–D are cross-sectional views of a pump mechanism adapted to pump fluid in both directions only by mechanically pushing a separate sealing wall portion 218 in one direction. FIG. 30A shows a piston 220 pushed forwards against a spring 222 towards the wall portion 218 and located in a pump housing 224 conducting fluid from a right upper fluid passage 226 of the housing 224 to a left fluid passage 228 of the housing 224. A main valve 230 is open and a nonreturn valve 232 is closed. FIG. 30B illustrates the first pump movement in which the piston 220 has moved forwards and reaches the wall portion 218. FIG. 30C illustrates how the piston 220 moves backwards by the action of the spring 222. The main valve 230 is now closed and the nonreturn valve 232 is open for fluid from the right upper passage 226. FIG. 30D illustrates how the piston 220 is moved further downwardly from its position according to FIG. 30B while pushing the wall portion 218 downwardly against a second spring 234 that is stronger than spring 222, so that fluid escapes from a right lower fluid passage 236. When moving the piston 220 backwards from the position of FIG. 30D, fluid enters the left fluid passage 228 and a valve 238 in the lower right fluid passage 236 closes.

Figure 29D:
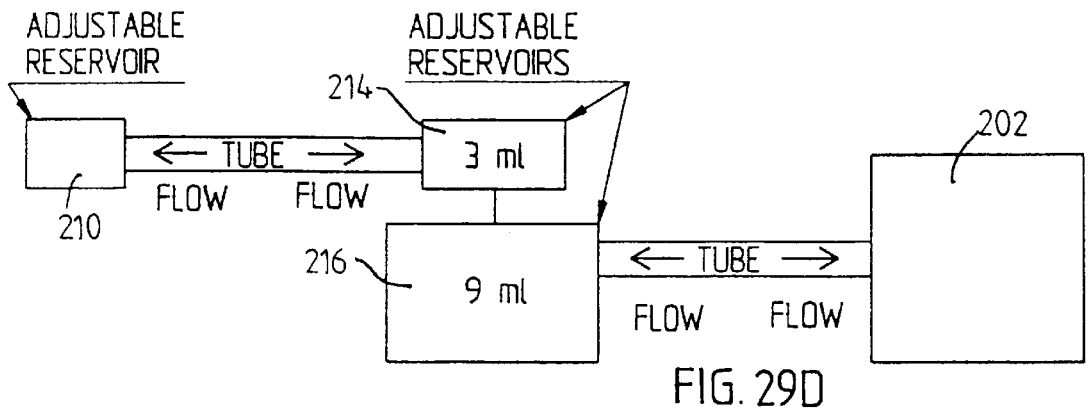
Figure 30D:
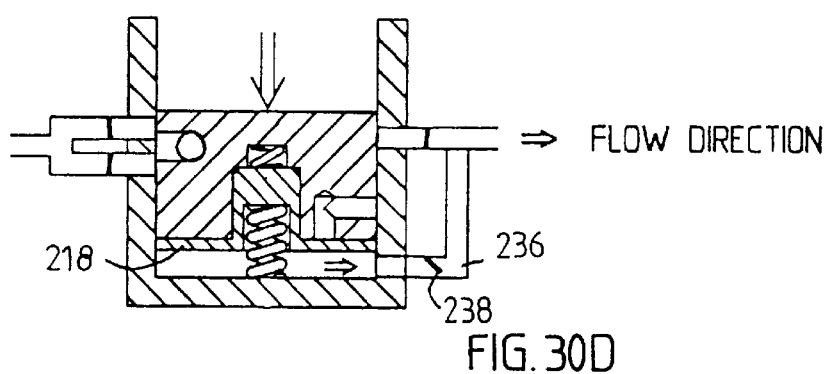

FIG. 31 is a cross-sectional view of a reservoir 240 defining a chamber 242, the size of which is variable and is controlled by a remote controlled motor 244, in accordance with FIG. 29B or 29D. The reservoir 240 and the motor 244 are placed in a housing 246. The chamber 242 is varied by moving a large wall 248. The wall 248 is secured to a nut 250, which is threaded on a rotatable spindle 252. The spindle 252 is rotated by the motor 244 via an angular gearing, which comprises two conical gear wheels 254 and 256 in mesh with each other. The motor 244 is powered by a battery 258 placed in the housing 246. A signal receiving means 260 for controlling the motor 244 is also placed in the housing 246. Alternatively, the battery 258 and the signal receiving means 260 may be mounted in a separate place. The signal receiving means 260 may comprise and known or conventional device which is capable of receiving a control signal and then operating the motor 244.

FIG. 32 is a cross-sectional view of a reservoir 262 defining a chamber 264, the size of which is variable and is controlled by manual manipulation. A gable wall portion 266 of an open ended inner cylindrical housing 68 is adapted to be pushed downwardly to fit in a desired locking groove 270 of a plurality of locking grooves 270 on the mantle wall of the cylindrical housing 268, to reduce the size of the chamber 64. The inner cylindrical housing 268 is suspended by springs 272 and is telescopically applied on an outer cylindrical housing 274. When pushing the inner cylindrical housing 268 it moves downwardly relative to the outer cylindrical housing 274 causing the gable wall portion 266 to release from the locking groove 270 and move upwardly relative to the inner cylindrical housing 268. When the inner housing 268 is moved upwardly by the action of the springs 272 the size of the chamber 264 is increased.

FIGS. 33A and 33B show a servo means comprising a main ring-shaped fluid reservoir 276 defining a chamber 278, the size of which is variable. Centrally positioned in the main ring-shaped reservoir 276 there is a servo fluid reservoir 280 defining a chamber 282, the size of which is variable. The chamber 282 of the servo reservoir 280 is significantly smaller than the chamber 278 of the main reservoir 276 (e.g. 0.05–0.5 times the size, or any level therebetween). The two reservoirs 276 and 280 are situated between two opposite separate walls 284 and 286, and are secured thereto. When changing the amount of fluid in the servo reservoir 280, the two opposite walls 284,286 are moved towards or away from each other, whereby the size of the chamber 278 of the main reservoir 276 is changed.

Figure 34:
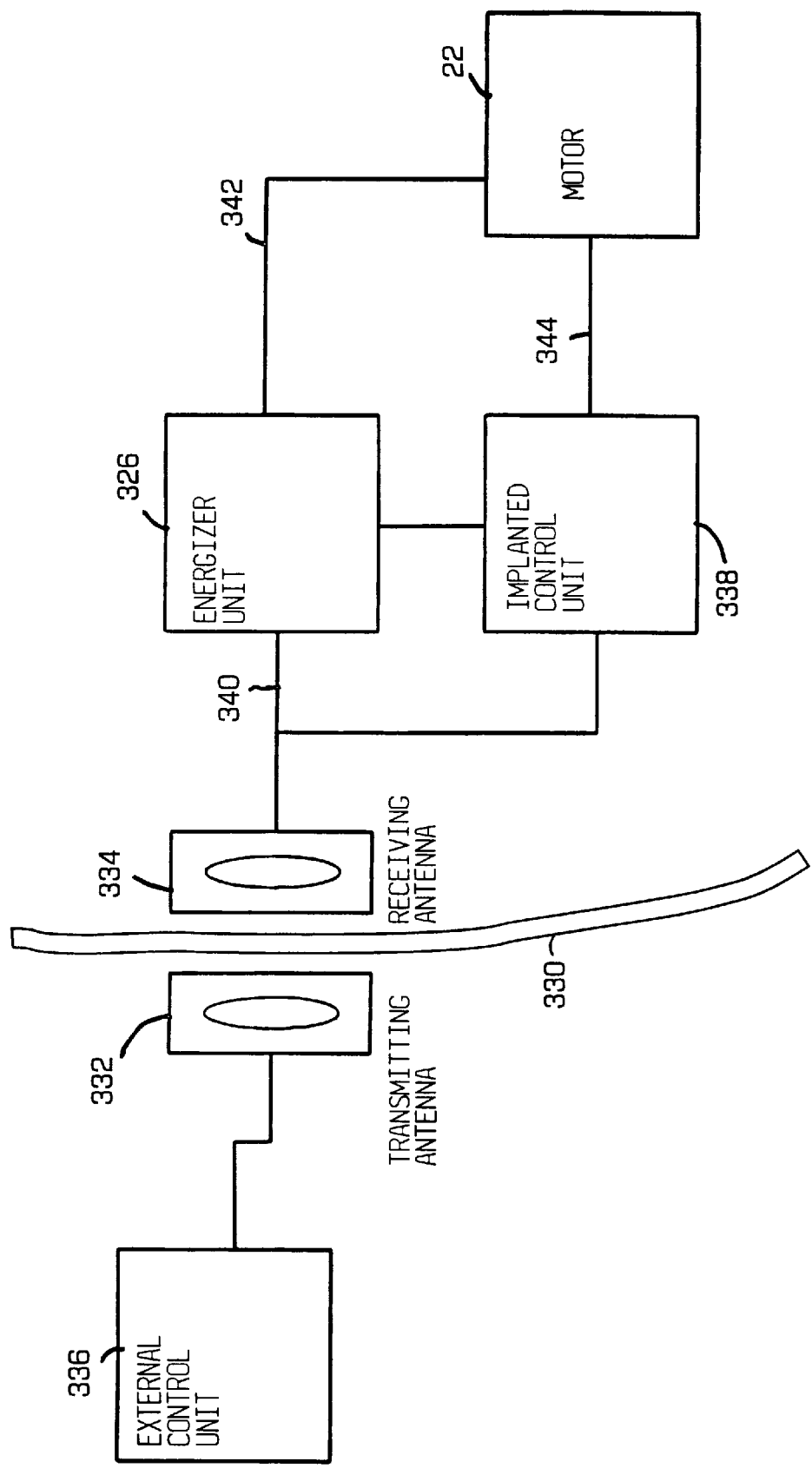
FIG. 34 is a block diagram illustrating remote control components of an exemplary device according to the invention.

FIG. 34 shows the basic parts of a remote control system of the device of the invention including a motor, for instance the electric motor 22. The remote control system is based on the transmission of electromagnetic wave signals, often of high frequencies in the order of 100 kHz–1 gHz, through the skin 330 of the patient. In FIG. 34, all parts placed to the left of the skin 330 are located outside the patient's body and all parts placed to the right of the skin 330 are implanted in the patient's body.

An external signal transmitting antenna 332 is to be positioned close to a signal receiving antenna 334 implanted in the patient's body close to the skin 330. As an alternative, the receiving antenna 334 may be placed for example inside the abdomen of the patient. The receiving antenna 334 comprises a coil, approximately 1–100 mm, preferably 25 mm in diameter, wound with a very thin wire and tuned with a capacitor to a specific high frequency. A small coil is chosen if it is to be implanted under the skin 330 of the patient and a large coil is chosen if it is to be implanted in the abdomen of the patient. The transmitting antenna 332 comprises a coil having about the same size as the coil of the receiving antenna 334 but wound with a thick wire that can handle the larger currents that is necessary. The coil of the transmitting antenna 332 is tuned to the same specific high frequency as the coil of the receiving antenna 334.

An external control unit 336 preferably comprises a microprocessor, a high frequency electromagnetic wave signal generator and a power amplifier. The microprocessor of the control unit 336 is adapted to switch on/off the generator and to modulate signals generated by the generator to send digital information via the power amplifier and the antennas 332, 334 to an implanted control unit 338. To avoid that accidental random high frequency fields trigger control commands, digital signal codes are used. A conventional keypad placed on the external control unit 336 is connected to the microprocessor thereof. The keypad is used to order the microprocessor to send digital signals to either increase or decrease the size of the restriction opening 3 defined by the loop of the restriction member (e.g. as described above). The microprocessor starts a command by applying a high frequency signal on the antenna 332. After a short time, when the signal has energized the implanted parts of the control system, commands are sent to increase or decrease the size of the restriction opening of the restriction member in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously over a relatively long time period (e.g. 30 seconds or more). When a new increase or decrease step is desired the Count byte is increased by one to allow the implanted control unit 338 to decode and understand that another step is demanded by the external control unit 336. If any part of the digital packet is erroneous, its content is simply ignored.

Through a line 340, an implanted energizer unit 326 draws energy from the high frequency electromagnetic wave signals received by the receiving antenna 334. The energizer unit 326 stores the energy in a power supply, such as a large capacitor, powers the control unit 338 and powers the electric motor 22 via a line 342.

The control unit 338 comprises a demodulator and a microprocessor. The demodulator demodulates digital signals sent from the external control unit 336. The microprocessor of the control unit 338 receives the digital packet, decodes it and, provided that the power supply of the energizer unit 326 has sufficient energy stored, sends a signal via a signal line 344 to the motor 22 to either increase or decrease the size of the restriction opening 3 of the restriction member depending on the received command code.

Alternatively, the energy stored in the power supply of the energizer unit may only be used for powering a switch, and the energy for powering the motor 22 may be obtained from another implanted power source of relatively high capacity, for example a battery. In this case the switch is adapted to connect the battery to the control unit 338 in an "on" mode when the switch is powered by the power supply and to keep the battery disconnected from the control unit in a "standby" mode when the switch is unpowered.

Figure 35:
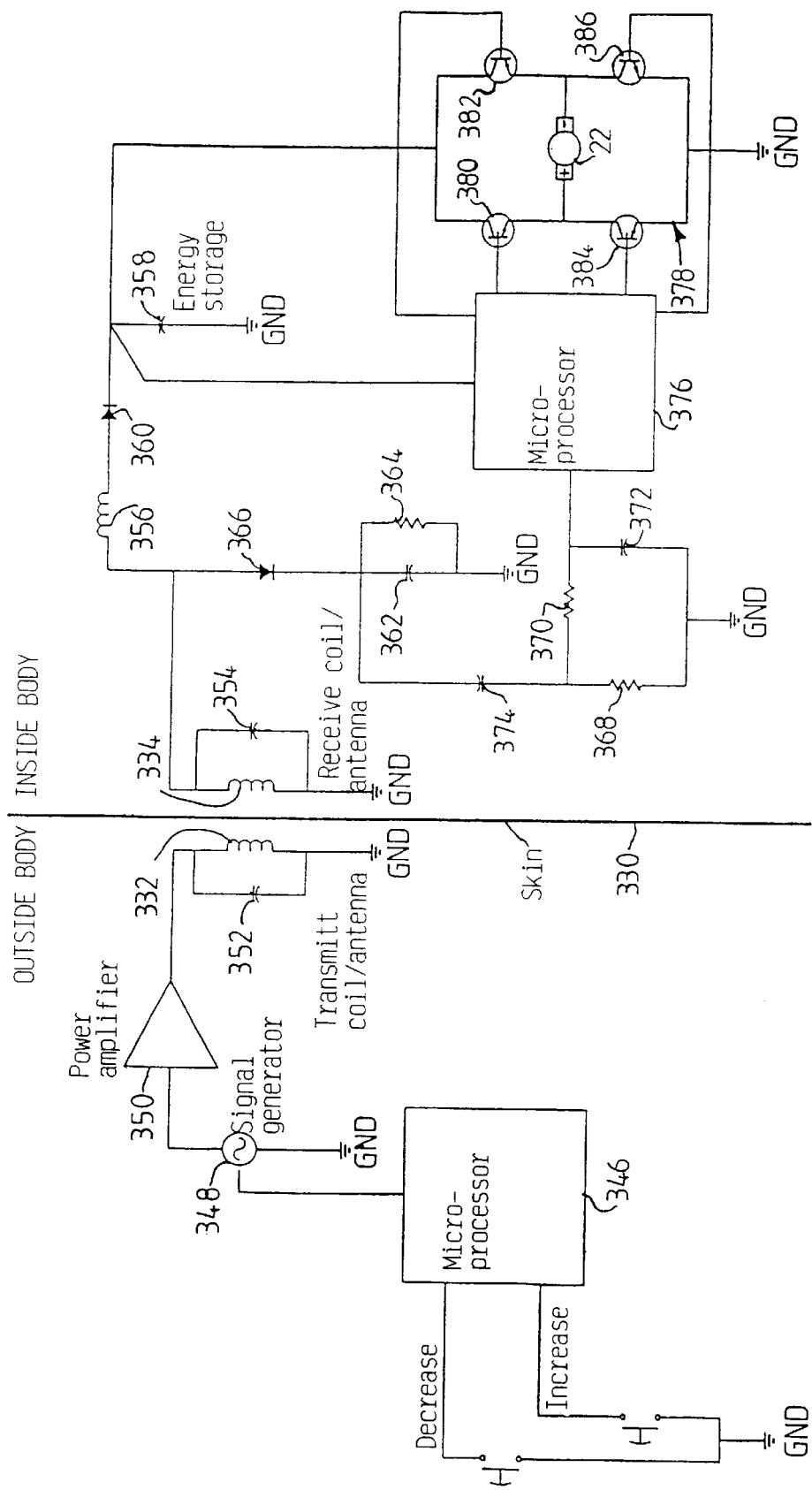
FIG. 35 is a schematic view of exemplary circuitry used for the system of the block diagram of FIG. 34.

With reference to FIG. 35, the remote control system schematically described above will now be described in accordance with a more detailed embodiment. The external control unit 336 comprises a microprocessor 346, a signal generator 348 and a power amplifier 350 connected thereto. The microprocessor 346 is adapted to switch the signal generator 348 on/off and to modulate signals generated by the signal generator 348 with digital commands that are sent to implanted components of the food intake restriction device. The power amplifier 350 amplifies the signals and sends them to the external signal transmitting antenna 332. The antenna 332 is connected in parallel with a capacitor 352 to form a resonant circuit tuned to the frequency generated by the signal generator 348.

The implanted signal receiving antenna coil 334 forms together with a capacitor 354 a resonant circuit that is tuned to the same frequency as the transmitting antenna 332. The signal receiving antenna coil 334 induces a current from the received high frequency electromagnetic waves and a rectifying diode 360 rectifies the induced current, which charges a storage capacitor 358. A coil 356 connected between the antenna coil 334 and the diode 360 prevents the capacitor 358 and the diode 360 from loading the circuit of the signal receiving antenna 334 at higher frequencies. Thus, the coil 356 makes it possible to charge the capacitor 358 and to transmit digital information using amplitude modulation.

A capacitor 362 and a resistor 364 connected in parallel and a diode 366 forms a detector used to detect amplitude modulated digital information. A filter circuit is formed by a resistor 368 connected in series with a resistor 370 connected in series with a capacitor 372 connected in series with the resistor 368 via ground, and a capacitor 374, one terminal of which is connected between the resistors 368, 370 and the other terminal of which is connected between the diode 366 and the circuit formed by the capacitor 362 and resistor 364. The filter circuit is used to filter out undesired low and high frequencies. The detected and filtered signals are fed to an implanted microprocessor 376 that decodes the digital information and controls the motor 22 via an H-bridge 378 comprising transistors 380,382,384 and 386. The motor 22 can be driven in two opposite directions by the H-bridge 378.

The microprocessor 376 also monitors the amount of stored energy in the storage capacitor 358. Before sending signals to activate the motor 22, the microprocessor 376 checks whether the energy stored in the storage capacitor 358 is enough. If the stored energy is not enough to perform the requested operation, the microprocessor 376 waits for the received signals to charge the storage capacitor 358 before activating the motor 22.

There are a number of other conceivable alternative embodiments of the invention that give the same result as the above-described embodiments. For example, the microprocessor of the external and implanted, respectively, control unit may be replaced by discrete components. The power amplifier of the external control unit may be omitted if the signals generated by the signal generator are strong enough. Therefore the invention is to be accorded the broadest interpretation of the appended claims to encompass all equivalent structures, assemblies, and methods.

What is claimed is:

1. A food intake restriction device for surgical application in the abdomen of a patient for forming a stoma opening in the stomach or esophagus of the patient, the device comprising:
    an elongated non-inflatable restriction member,
    forming means for forming said elongated restriction member into at least a substantially closed loop around the stomach or the esophagus, said loop defining a restriction opening, and
    a post-operation non-invasive adjustment device which mechanically adjusts said restriction member in said loop to change the size of said restriction opening.

2. The device according to claim 1, wherein said adjustment device adjusts said longitudinal extension of said elongated restriction member in said loop.

3. The device according to claim 2, wherein said restriction member comprises a main portion and two elongated end portions, and said adjustment device establishes a longitudinal relative displacement between said end portions of said restriction member, so that the size of said restriction opening is adjusted.

4. The device according to claim 3, wherein said adjustment device comprises a movement transferring member in engagement with at least one of said end portions of said restriction member and operable to displace said one end portion relative to said other end portion of said restriction member; wherein the movement transferring member comprises a drive wheel; and wherein said drive wheel is in engagement with both of said end portions of said restriction member and is operable to displace said end portions relative to each other; and further comprising an elongated flexible drive shaft operatively connected to said drive wheel; and further comprising a motor remote from said restriction member, said elongated flexible drive shaft operatively connecting said motor to said drive wheel; and wherein said drive wheel comprises a pulley in frictional engagement with said restriction member; and wherein a gear rack is formed on at least one of said end portions of said restriction member and said drive wheel comprises a gear wheel in mesh with said gear rack; and wherein said movement transferring member comprises at least one cylinder and a piston, which is movable therein and is connected to one of said end portions of said restriction member, said piston being operable to longitudinally displace said one end portion of said restriction member relative to said other end portion of said restriction member; and wherein said movement transferring means may comprise two interconnected cylinders and two pistons in said respective cylinders connected to said end portions, respectively, of said restriction member, said pistons being operable to longitudinally displace said end portions of said restriction member relative to each other; and further comprising a motor, which is fixed relative to said main portion of said restriction member and has a rotating drive shaft operatively connected to said movement transferring member, said motor being positioned relative to said elongated restriction member so that said drive shaft extends transverse thereto, or substantially tangentially to said loop of said restriction member.

5. The device according to claim 2, wherein said elongated restriction member is longitudinally resilient and said adjustment device comprises a contraction means which longitudinally contracts said resilient restriction member; and wherein said elongated restriction member comprises a substantially nonresilient main portion and an end portion forming an elongated helical spring, which is contractable by said contraction means; and wherein said contraction means comprises an elongated flexible pulling member connected to said main portion of said restriction member and extending through said helical spring to contract said helical spring against an arresting member, which is fixed relative to said main portion of said restriction member; and further comprising an elongated tube joined at one end thereof to said arresting member, said pulling member extending in said tube; and further comprising a motor remote from said restriction member and attached to said other end of said elongated tube, said motor being adapted to pull said pulling member through said tube to contract said helical spring.

6. The device according to claim 2, wherein said restriction member comprises an elongated helical spring having a free end, and a body to which said spring is nonrotatably secured at its opposite end, said adjustment device rotates said helical spring in one direction to enlarge said coils of said helical spring to longitudinally contract said elongated helical spring and to rotate said helical spring in said opposite direction to reduce said size of said coils of said helical spring to longitudinally extend said helical spring; and wherein said restriction member comprises a further elongated helical spring having a free end and nonrotatably secured to said body at its opposite end, and said adjustment device comprises a drive shaft having two opposite end portions connected to said helical springs, respectively, at their free ends, said helical coils forming left and right hand helices, respectively, or said adjustment device comprises a gearing having an input shaft and two opposite aligned output shafts connected to said helical springs, respectively, at their free ends, said input shaft being connected to said output shafts such that said output shafts rotate in said opposite directions upon rotation of said input shaft, said helical coils forming said same helices.

7. The device according to claim 1, wherein said restriction member forms a radially innermost circumferential confinement surface in said loop of said restriction member, and said adjustment device mechanically adjusts said restriction member so that at least a portion of said confinement surface is substantially radially displaced in said loop.

8. The device according to claim 7 wherein said restriction member comprises an elongated voltage responsive element forming part of said confinement surface and capable of bending into a bow in response to a voltage applied across said element, said radius of curvature of said bow being adjustable by changing said level of said voltage, or said restriction member comprises an elastic annular element forming said confinement surface, and said adjustment means is adapted to change said diameter of said elastic annular element in which case said forming means comprises a substantially rigid outer annular element coaxially surrounding said elastic annular element, and said adjustment device comprises means for pulling said elastic annular element radially outwardly towards said outer annular element to expand said elastic annular element, and said pulling means comprises a plurality of threads secured to said elastic annular element along said circumference thereof and running from said elastic element via guide members attached to said outer annular element; or wherein said forming means comprises a substantially rigid outer annular element, and said restriction member comprises an elongated helical spring extending internally along said outer annular element and contacting said latter, said helical spring forming part of said circumferential confinement surface and having a free end, and a body to which said spring is nonrotatably secured at its opposite end, said adjustment device rotating said helical spring in one direction to enlarge said coils of said helical spring to contract said circumferential confinement surface and rotating said helical spring in said opposite direction to reduce the size of said coils of said helical spring to expand said circumferential confinement surface, or said forming means comprises a substantially rigid outer annular element, and said restriction member comprises a first and a second elongated helical spring extending internally along said outer annular element and contacting the latter, said helical springs forming part of said circumferential confinement surface, said first and said second spring, respectively, having a free end, and a body to which said first and said second spring, respectively, is nonrotatably secured at its opposite end, said adjustment device rotating said first and said second spring, respectively, in one direction to enlarge said coils of said spring to contract said circumferential confinement surface and rotating said first and said second spring, respectively, in said opposite direction to reduce the size of said coils of said spring to expand said circumferential confinement surface.

9. The device according to claim 1, wherein said restriction member comprises at least two separate elements, at least one of which is pivoted so that it may turn in a plane in which said loop of said restriction member extends, and said adjustment device turns said pivoted element to change the size of said restriction opening; and wherein said restriction member comprises a plurality of separate pivoted elements disposed in series, each pivoted element being turnable in said plane, and said adjustment device turns all of said pivoted elements to change the size of said restriction opening; and wherein said pivoted elements comprise lamellae arranged like said adjustable aperture mechanism of a camera.

10. The device according to claim 1, wherein said restriction member comprises at least two frame elements which are foldable towards each other by said adjustment device; and wherein said foldable frame elements comprise two substantially semi-circular frame elements which are hinged together such that said semi-circular elements are swingable relative to each other from a fully open state in which they form a circle to a fully folded state in which they form a semi-circle.

11. The device according to claim 1, wherein said elongated restriction member is elastic and varies in thickness as seen in a cross-section therethrough, and said adjustment device turns the restriction member around said longitudinal extension thereof; and wherein said elongated restriction member comprises an elastic belt.

12. The device according to claim 1, further comprising a motor operatively connected to said adjustment device; and wherein said motor is fixed to said restriction member, or said motor is remote from said restriction member and is connected to said adjustment device by a power transmission conduit, such as a flexible power transmission conduit; and wherein said motor is a manually activatable electric motor.

13. The device according to claim 1, further comprising a hydraulic device which operates said adjustment device; and wherein said hydraulic device is manually activatable or is powered by an electric motor, such as a manually activatable electric motor; and further comprising a reservoir containing a predetermined amount of fluid for supplying said hydraulic device with fluid; and wherein said reservoir defines a chamber for said predetermined amount of fluid and said hydraulic device changes he size of said chamber; and wherein said hydraulic device comprises first and second wall portions of said reservoir, which are displaceable relative to each other to change the size of said chamber of said reservoir; and wherein said first and second wall portions of said reservoir are designed to be displaceable relative to each other by manual manipulation thereof; and wherein said first and second wall portions of said reservoir are displaceable relative to each other by manually pushing, pulling or rotating any of said wall portions in one direction, or wherein said first and second wall portions of said reservoir are displaceable relative to each other by magnetic means, or wherein said first and second wall portions of said reservoir are displaceable relative to each other by hydraulic means, or wherein said first and second wall portions of said reservoir are designed to be displaceable relative to each other by electric control means such as an electric motor; and wherein said hydraulic device is adapted to operate said adjustment device with fluid from said reservoir in response to a predetermined first displacement of said first wall portion of said reservoir relative to said second wall portion of said reservoir, to increase the size of said restriction opening, and to operate said adjustment device with fluid from said reservoir in response to a predetermined second displacement of said first wall portion of said reservoir relative to said second wall portion of said reservoir, to decrease the size of said restriction opening.

14. The device according to claim 13 further comprising a hydraulic fluid reservoir; and wherein said hydraulic device comprises an activatable pump for pumping fluid between said reservoir and said adjustment device; and wherein said pump comprises a first activation member for activating said pump means to pump fluid from said reservoir to said adjustment device and a second activation member for activating said pump to pump fluid from said adjustment device to said reservoir; and wherein said first and second activation members are operable by manual manipulation thereof or by magnetic means, or by hydraulic means, or by electric means such as an electric motor; and wherein each of said first and second activation members are operable by manually pushing, pulling or rotation thereof in one direction; and wherein at least one of said activation members operates when subjected to an external pressure exceeding a predetermined magnitude.

15. The device according to claim 14, wherein said hydraulic device comprises a servo means; wherein said hydraulic device comprises first and second wall portions of said reservoir, and said servo means is adapted to provide relative displacement between said first and second wall portions of reservoir; and wherein said servo means comprises magnetic means, electric means, or hydraulic means comprising a servo reservoir defining a chamber containing servo fluid and said hydraulic operation means comprises first and second wall portions of said servo reservoir, which are displaceable relative to each other to change the size of said chamber of said servo reservoir; in response to a first displacement of the first wall portion of said servo reservoir relative to the second wall portion of the same reservoir, decrease the restriction opening via an indirect control of the adjustment device, and with a second displacement of the first wall portion relative to the second wall portion increase the size of the restriction opening; and wherein said first and second wall portions of said servo reservoir are designed to be displaceable relative to each other by manual manipulation thereof, and wherein said first and second wall portions of said servo reservoir are designed to be displaceable relative to each other by manually pushing, pulling or rotating any of said wall portions of said servo reservoir in one direction; wherein first and second wall portions of said servo reservoir are displaceable relative to each other by magnetic means, or said first and second wall portions of said servo reservoir are displaceable relative to each other by hydraulic means, or said first and second wall portions of said servo reservoir are displaceable relative to each other by electric control means such as an electric motor.

16. The device according to claim 1, further comprising a wireless remote control means for controlling said adjustment device, said remote control means comprising a separate signal transmitting means and a signal receiving means adapted to control said adjustment device in response to signals received from said signal transmitting means, and a motor for operating said adjustment device and an energizer unit for providing energy, and wherein said signal receiving means comprises a control unit powering said motor with energy provided by said energizer unit in response to signals received from said signal transmitting means; and wherein said energizer unit comprises a power supply; and wherein said control unit is adapted to power said motor with energy from said power supply, and wherein said power supply is an electric power supply such as a battery and said motor is an electric motor.

17. The device according to claim 16 wherein said signal transmitting means transmits electromagnetic wave signals and said energizer unit draws radiant energy from said electromagnetic wave signals as they are transmitted to said signal receiving means and transfer said radiant energy into electric energy for powering said electric motor.

18. The device according to claim 16, wherein said energizer unit comprises a rechargeable electric power supply for storing said electric energy and said control unit powers said electric motor with energy from said rechargeable electric power supply in response to signals received from said signal transmitting means.

19. The device according to claim 18 wherein said electric power supply comprises a capacitor, and wherein said electric motor is a stepping motor.

20. The device according to claim 17, wherein said energizer unit comprises a battery, an electrically operable switch connecting said battery to said signal receiving means in an on mode when said switch is powered and to keep said battery disconnected from said signal receiving means in a standby mode when said switch is unpowered, and a rechargeable electric power supply for powering said switch; and wherein said control unit powers said electric motor with energy from said battery in response to signals received from said signal transmitting means, when said switch is in its on mode; and wherein said signal transmitting means transmits electromagnetic wave signals and said energizer unit draws radiant energy from said electromagnetic wave signals as they are transmitted to said signal receiving means and transfers said radiant energy into a current for charging said rechargeable electric power supply; and wherein said rechargeable electric power supply is a capacitor, or wherein said energizer unit comprises a coil connected to said signal receiving means for inducing an alternating current as electromagnetic wave signals are transmitted through said coil to said signal receiving means and a rectifier for rectifying said alternating current.

21. The device according to claim 2, wherein said forming means comprises a spring material forming said elongated restriction member into said loop, such that said restriction opening has a predetermined size, and said adjustment device adjusts said restriction member against said spring action of said spring material; and wherein said spring material is integrated in said restriction member.

22. The device according to claim 1, wherein said adjustment device comprise a servo means, such as a hydraulic device, an electric control means, or a magnetic means, or a manual manipulating means; and wherein said hydraulic device is activated by manual manipulating means, said electric control means is activated by manual manipulating means, and said magnetic means is activated by manual manipulating means.

23. The device according to claim 22 wherein said servo means comprises a hydraulic operation means comprising a servo reservoir and a fluid supply reservoir connected in a closed system and containing a predetermined amount of fluid, and wherein said fluid supply reservoir defines a chamber for said predetermined amount of fluid and said hydraulic operation means changes the size of said chamber and thereby controls said servo reservoir; and wherein said fluid supply reservoir comprises first and second wall portions of said fluid supply reservoir, which are displaceable relative to each other to change the size of said chamber; and wherein said first and second wall portions of said fluid supply reservoir are displaceable relative to each other by manual manipulation means for pushing, pulling or rotating any of said wall portions in one direction; or by magnetic means for pushing, pulling, or rotating any of said wall portions in one direction, or by electrical control means for pushing, pulling or rotating any of said wall portions in one direction, or by electrical control means for pushing, pulling or rotating any of said wall portions in one direction, or by hydraulic means for pushing, pulling or rotating any of said wall portions in one direction; and wherein said fluid supply reservoir operates said servo reservoir with fluid from said fluid supply reservoir in response to predetermined first displacement of the first wall portion of said fluid supply reservoir relative to said second wall portions of said fluid supply reservoir to increase said amount of fluid in said servo reservoir and to operate said servo reservoir in response to a predetermined second displacement of said first wall portion of said fluid supply reservoir relative to said second wall portion of said fluid supply reservoir to decrease the amount of fluid in the servo reservoir.

24. A method of treating morbid obesity, comprising:
  (a) surgically implanting in the abdomen of a patient with morbid obesity a food intake restriction device which forms a stoma opening in the stomach or esophagus, by forming an elongated non-inflatable restriction member into at least a substantially closed loop around the stomach or the esophagus of the patient, the loop defining a restriction opening; and then
  (b) when necessary for the patient's health or desired progress, in a non-invasive procedure mechanically adjusting the restriction member to change the size of the restriction opening.

25. A method as recited in claim 24 wherein (a) is practiced by implanting a restriction member comprising a main portion and two elongated end portions; and wherein (b) is practiced by establishing a longitudinal relative displacement between the end portions of the restriction member so that the size of the restriction opening is adjusted.

26. A method as recited in claim 24 wherein (a) is practiced by implanting a restriction member having a radially innermost circumferential confinement surface formed in the loop; and wherein (b) is practiced by causing at least a portion of the confinement surface to be radially displaced in the loop.

27. A method as recited in claim 24 wherein (a) is practiced by: (i) inflating the patient's abdomen with gas by penetration of the patient's skin, (ii) introducing at least one laparoscopic trocar into the abdomen to introduce the elongated restriction member and one or more medical instruments, and then (iii) forming the elongated restriction member into the at least substantially closed loop.

28. A surgical method for laparoscopically implanting a non-inflatable food restriction device for forming a stoma opening in the stomach or esophagus comprising:
  (a) insufflating the abdomen of a patient to form a pneumoperitoneum;
  (b) introducing at least one laparoscopic trocar into the abdomen;
  (c) using a dissecting tool inserted through the laparoscopic trocar, dissecting the region of the esophagus or stomach adjacent or above the bursa omentalis; and
  (d) introducing the non-inflatable food restriction device in the abdomen and applying the device in at least a substantially closed loop around the stomach or esophagus.

29. A method as recited in claim 28 further comprising, after (a)–(d), (e) post-operatively adjusting the restriction opening in a non-invasive procedure.

* * * * *